United States Patent
Nielsen et al.

(10) Patent No.: US 8,809,355 B2
(45) Date of Patent: Aug. 19, 2014

(54) GABA$_A$ RECEPTOR MODULATORS

(75) Inventors: Mogens Peter Cherly Nielsen, Roskilde (DK); Tommy Liljefors, Frederiksberg (DK); Jakob Alexander Nilsson, Lund (SE); Olov A Sterner, Malmö (SE)

(73) Assignee: Innovationspatent Sverige AB, Lund (SE)

( * ) Notice: Subject to any disclaimer, the term of this patent is extended or adjusted under 35 U.S.C. 154(b) by 967 days.

(21) Appl. No.: 12/936,050

(22) PCT Filed: Apr. 2, 2009

(86) PCT No.: PCT/SE2009/000176
§ 371 (c)(1),
(2), (4) Date: Dec. 10, 2010

(87) PCT Pub. No.: WO2009/123537
PCT Pub. Date: Oct. 8, 2009

(65) Prior Publication Data
US 2011/0092525 A1 Apr. 21, 2011

(30) Foreign Application Priority Data
Apr. 4, 2008 (SE) ........................ 0800759

(51) Int. Cl.
*A61K 31/519* (2006.01)
*C07D 487/04* (2006.01)

(52) U.S. Cl.
CPC ............ C07D 487/04 (2013.01); *A61K 31/519* (2013.01)
USPC .......................... 514/267; 544/251

(58) Field of Classification Search
CPC ............................ A61K 31/519; C07D 487/04
USPC .......................... 514/267; 544/251
See application file for complete search history.

(56) References Cited

U.S. PATENT DOCUMENTS 5,688,803 A 11/1997 Buttelmann et al.
6,268,496 B1 7/2001 Shaw

FOREIGN PATENT DOCUMENTS

| WO | 98/04559 A2 | 2/1998 | |
| WO | 99/18106 A1 | 4/1999 | |
| WO | WO 99/18106 * | 4/1999 | ........... C07D 487/04 |
| WO | 99/65907 A1 | 12/1999 | |
| WO | 01/92258 A1 | 12/2001 | |

OTHER PUBLICATIONS

International Preliminary Report on Patentability mailed Oct. 14, 2010: PCT/SE2009/000176.
International Search Report: PCT/SE2009/000176, (2009).
European Search Report: dated Apr. 9, 2011; Appln. No. 09 726 806.4.

* cited by examiner

*Primary Examiner* — Erich A Leeser
(74) *Attorney, Agent, or Firm* — Ladas & Parry LLP

(57) ABSTRACT

The present invention relates to novel compounds of the general formula (I) having anxiolytic, anticonvulsant, sedative-hypnotic and myorelaxant conditions as well as anxiogenic, somnolytic and convulsant conditions in mammals, including humans, as GABA$_A$ receptor modulator.

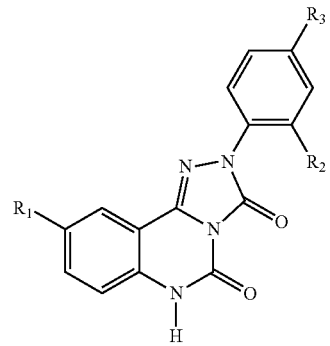

2 Claims, No Drawings

GABA$_A$ RECEPTOR MODULATORS

TECHNICAL FIELD

The present invention relates to novel GABA$_A$ receptor modulators, their use, pharmaceutical compositions comprising the same, as well as a method for treating anxiolytic, anticonvulsant, muscle relaxant and sedative-hypnotic conditions in mammals, including humans.

BACKGROUND OF THE INVENTION

One of the quantitatively major inhibitory neurotransmitter substances present in the central nervous system is γ-amino butyric acid (GABA).[i] It exerts its physiological effect through three different receptor types, the ligand gated chloride channels GABA$_A$ and GABA$_C$ and the G-protein coupled GABA$_B$ receptor.[ii] The GABA$_A$ receptor complex is a pentameric assembly of several different protein subunits, which exist in multiple isoforms ($\alpha_{1-6}$, $\beta_{1-4}$, $\gamma_{1-4}$, θ, π, ε, $\rho_{1-3}$ and δ).[iii] The most abundant of these GABA$_A$ receptors contain two α, two β and one γ subunits. Several ligands are known to allosterically modulate the GABA$_A$ receptor, such as benzodiazepine (BZD), barbiturates, ethanol and certain steroids.[i]

Historically, the BZD has attracted most attention and has as such been used clinically for treatment as anxiolytic, anti-convulsant, muscle relaxant and sedative-hypnotic drugs.[iv] Among the wide variety of nonbenzodiazepine ligands, the most potent and perhaps best studied belong to the following classes: 2-arylpyrazoloquinolines, β-carbolines, pyridodiindoles, pyrimidin-5(6H)-ones, triazoloqunioxalines, cyclopyrrolones, and quinolines. The pharmacological effect of subtype-selective substances has been studied with the use of transgenic mice. Recent studies clearly suggest that a particular pharmacological response is associated with an action at a receptor with a specific subtype composition e.g. $\alpha_1$-containing receptors are involved in sedation and anterograde amnesia, and $\alpha_2$-, and/or $\alpha_3$- in anxiolytic activity, and $\alpha_5$-containing receptors might be associated with cognition and memory.[v,vi] It is believed that the BZD receptor is situated between the α- and γ-subunits, and a pharmacophore model of the binding site has been created. The model has later been refined through a SAR study of synthetical flavones, which added additional pharmacophore elements to the model.[vii,viii]

SUMMARY OF THE PRESENT INVENTION

The present invention aims at preparing new active drugs being considerably more potent than the benzodiazepines hitherto known.

The refined model has been applied in the search of new non-benzodiazepine ligands and a series of new 4-quinolones with K$_i$ values down to 0.05 nM has been synthesized. In the present study focus has been laid on novel triazoloquinazolinone ligands developed through the pharmacophore model (Scheme 1). The new potent ligands resemble the 2-arylpyrazoloquinolines class of compound, superimpositioned with triazoloquinazoline 8a in Scheme 2. All together the triazoloquinazolinones seems to fulfill all requirements necessary for a strong BZD receptor affinity. In particular, the NH(6), N(1), and the 3- and 5-carbonylic oxygen are supposed to interact with the A$_2$, H$_2$ and H$_1$ in the pharmacophore model representation, respectively. The aim of this invention is to: firstly, develop novel triazoloquinazolinones, secondly a synthetic route to the triazoloquinazolinones and, thirdly to further explore the pharmacophore region called "interface". To facilitate the further investigation of the interface it has also been necessary to find suitable cross-coupling protocol, which has been applied to furnish the triazoloquinazolinone scaffold with suitable substituents pointing towards the interface region. A common feature amongst many previously prepared potent ligands substituted towards the interface, is a methylene or ethylene linker between the BZ ligand scaffold and the interface interacting residue.

DETAILED DESCRIPTION OF THE PRESENT INVENTION

The present invention in particular relates to novel compounds of the general formula (I)

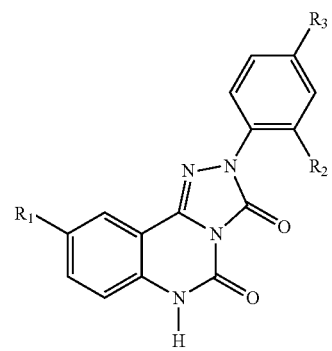

wherein
R$_1$ is selected from the group consisting of halogen, alkyl having 1 to 2 carbon atoms, carboxyalkyl having 1 to 3 carbon atoms, phenyl-alkynyl- having 2 to 3 carbon atoms in the alkynyl chain, phenyl-alkenyl- having 1 to 3 carbon atoms in the alkenyl chain, phenyl-alkyl-having 1-3 carbon atoms in the alkyl chain and wherein the phenyl moiety may be further substituted by an oxygen or a sulphur atom in any position, pyridyl-alkyl- having 1 to 2 carbon atoms in the alkyl chain, and trifluoromethyl,
R$_2$ is selected from the group consisting of hydrogen and halogen, and
R$_3$ is selected from the group consisting of hydrogen, halogen and alkyl having 1 to 2 carbon atoms, or pharmaceutically acceptable salts thereof.

In a preferred embodiment R$_1$ being halogen is selected from the group consisting of bromo, iodo, fluoro and chloro.

In a preferred embodiment R$_1$ being alkyl is selected from the group consisting of methyl and ethyl.

In a preferred embodiment R$_1$ being carboxyalkyl is selected from the group consisting of carboxymethyl, carboxyethyl and carboxypropyl.

In a preferred embodiment R$_1$ being phenylalkynyl is selected from the group consisting of phenylethynyl and phenyl-1-propynyl and phenyl-2-propynyl.

In a preferred embodiment R$_1$ being phenylalkenyl is selected from the group consisting of phenylethenyl, phenyl-1-propenyl and phenyl-2-propenyl.

In a preferred embodiment R$_1$ being phenylalkyl is selected from the group consisting of phenylmethyl, phenylethyl, phenylisopropyl and phenylpropyl.

In a preferred embodiment R$_2$ being halogen is selected from the group consisting of bromo, iodo, fluoro and chloro.

In a preferred embodiment R$_3$ being halogen is selected from the group consisting of bromo, iodo, fluoro and chloro.

In a preferred embodiment R$_3$ being alkyl is selected from the group consisting of methyl, ethyl propyl and isopropyl.

A further aspect of the invention relates to compounds of the general formula (I)

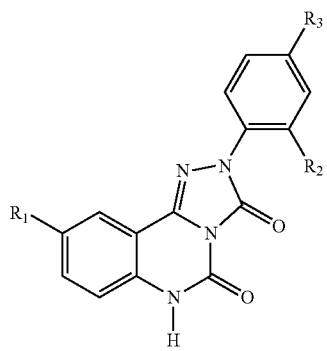

wherein
R₁ is selected from the group consisting of
halogen,
alkyl having 1 to 2 carbon atoms,
carboxyalkyl having 1 to 3 carbon atoms,
phenyl-alkynyl- having 2 to 3 carbon atoms in the alkynyl chain,
phenyl-alkenyl- having 1 to 3 carbon atoms in the alkenyl chain,
phenyl-alkyl- having 1-3 carbon atoms in the alkyl chain and wherein the phenyl moiety may be further substituted by an oxygen or a sulphur atom in any position,
pyridyl-alkyl- having 1 to 2 carbon atoms in the alkyl chain and
trifluoromethyl
R₂ is selected from the group consisting of
hydrogen and
halogen, and
R₃ is selected from the group consisting of
hydrogen,
halogen and
alkyl having 1 to 2 carbon atoms,
or pharmaceutically acceptable salts thereof for use in treating anxiolytic, anticonvulsant, sedative-hypnotic and myorelaxant conditions as well as anxiogenic, somnolytic and convulsant conditions.

In a preferred embodiment thereof R₁ being halogen is selected from the group consisting of bromo, iodo, fluoro and chloro.

In a preferred embodiment thereof R₁ being alkyl is selected from the group consisting of methyl and ethyl.

In a preferred embodiment thereof R₁ being carboxyalkyl is selected from the group consisting of carboxymethyl, carboxyethyl and carboxypropyl.

In a preferred embodiment thereof R₁ being phenylalkynyl is selected from the group consisting of phenylethynyl and phenyl-1-propynyl and phenyl-2-propynyl.

In a preferred embodiment thereof R₁ being phenylalkenyl is selected from the group consisting of phenylethenyl, phenyl-1-propenyl and phenyl-2-propenyl.

In a preferred embodiment thereof R₁ being phenylalkyl is selected from the group consisting of phenylmethyl, phenylethyl and phenylisopropyl and phenylpropyl.

In a preferred embodiment thereof R₂ being halogen is selected from the group consisting of bromo, iodo, fluoro and chloro.

In a preferred embodiment thereof R₃ being halogen is selected from the group consisting of bromo, iodo, fluoro and chloro.

In a preferred embodiment thereof R₃ being alkyl is selected from the group consisting of methyl, ethyl propyl and isopropyl.

A still further aspect of the invention relates to a pharmaceutical composition comprising as an active ingredient one or more of the compounds of the general formula (I)

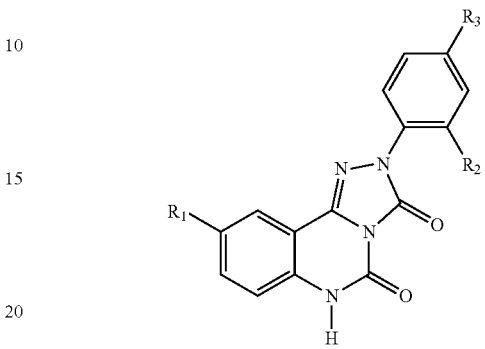

wherein
R₁ is selected from the group consisting of
halogen,
alkyl having 1 to 2 carbon atoms,
carboxyalkyl having 1 to 3 carbon atoms,
phenyl-alkynyl- having 2 to 3 carbon atoms in the alkynyl chain,
phenyl-alkenyl- having 1 to 3 carbon atoms in the alkenyl chain,
phenyl-alkyl- having 1-3 carbon atoms in the alkyl chain and wherein the phenyl moiety may be further substituted by an oxygen or a sulphur atom in any position,
pyridyl-alkyl- having 1 to 2 carbon atoms in the alkyl chain, and
trifluoromethyl
R₂ is selected from the group consisting of
hydrogen and
halogen, and
R₃ is selected from the group consisting of
hydrogen,
halogen and
alkyl having 1 to 2 carbon atoms,
or pharmaceutically acceptable salts thereof in combination with one or more excipients.

In a preferred embodiment thereof R₁ being halogen is selected from the group consisting of bromo, iodo, fluoro and chloro.

In a preferred embodiment thereof R₁ being alkyl is selected from the group consisting of methyl and ethyl.

In a preferred embodiment thereof R₁ being carboxyalkyl is selected from the group consisting of carboxymethyl, carboxyethyl and carboxypropyl.

In a preferred embodiment thereof R₁ being phenylalkynyl is selected from the group consisting of phenylethynyl and phenyl-1-propynyl and phenyl-2-propynyl.

In a preferred embodiment thereof R₁ being phenylalkenyl is selected from the group consisting of phenylethenyl, phenyl-1-propenyl and phenyl-2-propenyl.

In a preferred embodiment thereof R₁ being phenylalkyl is selected from the group consisting of phenylmethyl, phenylethyl and phenylisopropyl and phenylpropyl.

In a preferred embodiment thereof R₂ being halogen is selected from the group consisting of bromo, iodo, fluoro and chloro.

In a preferred embodiment thereof $R_3$ being halogen is selected from the group consisting of bromo, iodo, fluoro and chloro.

In a preferred embodiment thereof $R_3$ being alkyl is selected from the group consisting of methyl, ethyl propyl and isopropyl.

A further aspect of the invention relates to a method for treating anxiolytic, anticonvulsant, sedative-hypnotic and myorelaxant conditions as well as anxiogenic, somnolytic and convulsant conditions in mammals, including humans, by administering a therapeutically effective amount of one or more of the compounds of the general formula (I)

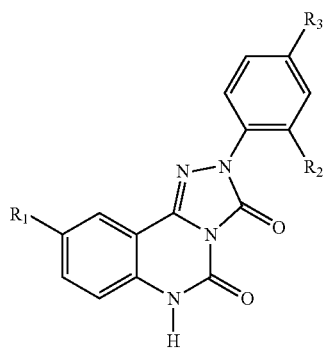

wherein
$R_1$ is selected from the group consisting of
halogen,
alkyl having 1 to 2 carbon atoms,
carboxyalkyl having 1 to 3 carbon atoms,
phenyl-alkynyl- having 2 to 3 carbon atoms in the alkynyl chain,
phenyl-alkenyl- having 1 to 3 carbon atoms in the alkenyl chain,
phenyl-alkyl- having 1-3 carbon atoms in the alkyl chain and wherein the phenyl moiety may be further substituted by an oxygen or a sulphur atom in any position,
pyridyl-alkyl- having 1 to 2 carbon atoms in the alkyl chain and
trifluoromethyl
$R_2$ is selected from the group consisting of
hydrogen and
halogen, and
$R_3$ is selected from the group consisting of
hydrogen,
halogen and
alkyl having 1 to 2 carbon atoms,
or pharmaceutically acceptable salts thereof.

In a preferred embodiment thereof $R_1$ being halogen is selected from the group consisting of bromo, iodo, fluoro and chloro.

In a preferred embodiment thereof $R_1$ being alkyl is selected from the group consisting of methyl and ethyl.

In a preferred embodiment thereof $R_1$ being carboxyalkyl is selected from the group consisting of carboxymethyl, carboxyethyl and carboxypropyl.

In a preferred embodiment thereof $R_1$ being phenylalkynyl is selected from the group consisting of phenylethynyl and phenyl-1-propynyl and phenyl-2-propynyl.

In a preferred embodiment thereof $R_1$ being phenylalkenyl is selected from the group consisting of phenylethenyl, phenyl-1-propenyl and phenyl-2-propenyl.

In a preferred embodiment thereof $R_1$ being phenylalkyl is selected from the group consisting of phenylmethyl, phenylethyl and phenylisopropyl and phenylpropyl.

In a preferred embodiment thereof $R_2$ being halogen is selected from the group consisting of bromo, iodo, fluoro and chloro.

In a preferred embodiment thereof $R_3$ being halogen is selected from the group consisting of bromo, iodo, fluoro and chloro.

In a preferred embodiment thereof $R_3$ being alkyl is selected from the group consisting of methyl, ethyl propyl and isopropyl.

The term "pharmaceutically acceptable salt" means either an acid addition salt or a basic addition salt which is compatible with the treatment of patients. A "pharmaceutically acceptable acid addition salt" is any non-toxic organic or inorganic acid addition salt of the base compounds represented by Formula I or any of its intermediates. Illustrative inorganic acids which form suitable salts include hydrochloric, hydrobromic, sulfuric and phosphoric acid and acid metal salts such as sodium monohydrogen orthophosphate and potassium hydrogen sulfate. Illustrative organic acids which form suitable salts include the mono-, di- and tricarboxylic acids. Illustrative of such acids are, for example, acetic, glycolic, lactic, pyruvic, malonic, succinic, glutaric, fumaric, malic, tartaric, citric, ascorbic, maleic, hydroxymaleic, benzoic, hydroxybenzoic, phenylacetic, cinnamic, salicylic, 2-phenoxybenzoic, p-toluenesulfonic acid and other sulfonic acids such as methanesulfonic acid and 2-hydroxyethanesulfonic acid. Either the mono- or di-acid salts can be formed, and such salts can exist in either a hydrated, solvated or substantially anhydrous form. In general, the acid addition salts of these compounds are more soluble in water and various hydrophilic organic solvents, and generally demonstrate higher melting points in comparison to their free base forms. The selection criteria for the appropriate salt will be known to one skilled in the art. Other non-pharmaceutically acceptable salts e.g. oxalates may be used for example in the isolation of compounds of Formula I for laboratory use, or for subsequent conversion to a pharmaceutically acceptable acid addition salt.

A "pharmaceutically acceptable basic addition salt" is any non-toxic organic or inorganic base addition salt of the acid compounds represented by Formula I or any of its intermediates. Illustrative inorganic bases which form suitable salts include lithium, sodium, potassium, calcium, magnesium or barium hydroxides. Illustrative organic bases which form suitable salts include aliphatic, alicyclic or aromatic organic amines such as methylamine, trimethyl amine and picoline or ammonia. The selection of the appropriate salt may be important so that an ester functionality, if any, elsewhere in the molecule is not hydrolyzed. The selection criteria for the appropriate salt will be known to one skilled in the art.

"Solvate" means a compound of Formula I or the pharmaceutically acceptable salt of a compound of Formula I wherein molecules of a suitable solvent are incorporated in a crystal lattice. A suitable solvent is physiologically tolerable at the dosage administered as the solvate. Examples of suitable solvents are ethanol, water and the like. When water is the solvent, the molecule is referred to as a hydrate. The term "stereoisomers" is a general term for all isomers of the individual molecules that differ only in the orientation of their atoms in space. It includes mirror image isomers (enantiomers), geometric (cis/trans) isomers and isomers of compounds with more than one chiral centre that are not mirror images of one another (diastereomers).

The term "treat" or "treating" means to alleviate symptoms, eliminate the causation of the symptoms either on a temporary or permanent basis, or to prevent or slow the appearance of symptoms of the named disorder or condition.

The term "therapeutically effective amount" means an amount of the compound which is effective in treating the named disorder or condition.

The term "pharmaceutically acceptable carrier" means a non-toxic solvent, dispersant, excipient, adjuvant or other material which is mixed with the active ingredient in order to permit the formation of a pharmaceutical composition, i.e., a dosage form capable of administration to the patient. One example of such a carrier is a pharmaceutically acceptable oil typically used for parenteral administration.

It will be understood by those of skill in the art that when compounds of the present invention contain one or more chiral centers, the compounds of the invention may exist in, and be isolated as, enantiomeric or diastereomeric forms, or as a racemic mixture. The present invention includes any possible enantiomers, diastereomers, racemates or mixtures thereof, of a compound of formula I. The optically active forms of the compound of the invention may be prepared, for example, by chiral chromatographic separation of a racemate or chemical or enzymatic resolution methodology, by synthesis from optically active starting materials or by asymmetric synthesis based on the procedures described thereafter.

It will also be appreciated by those of skill in the art that certain compounds of the present invention may exist as geometrical isomers, for example E and Z isomers of alkenes. The present invention includes any geometrical isomer of a compound of formula I. It will further be understood that the present invention encompasses tautomers of the compounds of formula I.

It will also be understood by those skilled in the art that certain compounds of the present invention may exist in solvated, for example hydrated, as well as unsolvated forms. It will further be understood that the present invention encompasses all such solvated forms of the compounds of formula I.

Chemistry

All triazoloquinazolinone derivative investigated in this study are to the present knowledge all novel compounds. The triazoloquinazolinone scaffold 8a-e has been synthesized using two different synthetic routes as outlined in Scheme 9 and 2. The route leading to the bromo-substituted triazoloquinazolinone 8a-d via nitrotriazole 6 was optimized in terms easy multi-gram scale synthesis and hence avoids chromatography as mean of purification for the rather poorly soluble intermediates.

The quinazolinone scaffold in compound 4a and 4b has previously been synthesized in moderate yields by the addition of isothiocyanates or equivalent to anthranilic acids. In order to enhance yield and ease purification, an alternative synthetic route was developed utilizing an addition of ethoxycarbonyl isothiocyanate to anthranilic acids followed by cyclization in acetic anhydride and de-protection of the ethoxycarbonyl group with sodium methoxide, in excellent yield. Compound 4a and 4b was then treated with one equivalent of sodium methoxide and iodomethane, subsequently, to give 5a and 5b. The activation of the quinazolinone for the subsequent $S_NAr$ displacement was when achieved using two different protocols. Treatment of 5a with 3-nitro-1H-1,2,4-triazole in $I_2$/PPh$_3$/EtN(i-Pr)$_2$/toluene gave nitro-triazole derivative 6. Triazole derivative 7a-d was then prepared in a one-pot reaction by the treatment of 6 with 10a-d under solvent free conditions, in good yields. Alternatively, the activation of 5a and 5b was done with phosphorous oxychloride to give compound 11a and 11b, respectively. Condensation of 11a with 10b gave 7b, and condensation of 11b with 10b gave 7e in good yield. Under slightly modified conditions intermediate 12 could be isolated and subsequently cyclized to give 7e in a yield similar to the above one-pot reaction. Treatment of 7a-e with m-CPBA yielded 8a-e in a quantitative yield and a total yield of 49% over 7 steps. Compound 10a-d was prepared utilizing a Goldberg reaction between ethyl carbazate and substituted iodobenzenes in presences of cuprous iodide and 1,10-phenantroline as catalyst system. Reaction with unsubstituted and methyl-substituted iodobenzenes gave 10a and b in good yield, respectively, whereas substitution with electron withdrawing chloro- or fluoro-groups resulted in significantly lower yields. The triazoloquinazolinone 8a was applied to various cross-coupling reactions including copper free Sonigashira couplings, Stille couplings and a Heck coupling as shown in Scheme 3. The copper free Sonigashira coupling was applied for the synthesis of acetylenes 13a-f. The yield of these reactions is generally somewhat hampered by the problems associated with chromatographic purification of the planar rather insoluble biaryl acetylenes. Hydrogen reduction over palladium on coal yielded the desired ethylene-linked biaryls 14a-f, in a good yield. Stille-reagents 15a, b and c were synthesized by treatment of arylmethyl bromides (i.e. benzyl bromide, 3-fluorobenzyl bromide and thienyl bromide, respectively), with magnesium turnings and addition of tributyltin chloride to the resultant Gringard solution. Reaction with the 3-thienyl Gringard reagent led to formation of two products, of which the desired 15c was the major product. The high reactivity of the 2-position in 3-thienylmagnesium bromide has previously been exploit in the synthesis of 3-methyl-2-thenoic acid through the addition of carbon dioxide to the Gringard reagent. Stille coupling between 8a and 15a-c yielded the methylene-linked biaryls 16a-c in good yields. A Heck reaction with benzyl acrylate gave compound 17 in a good yield. Subsequent hydrogen reduction over palladium on charcoal gave carboxylic acid 18 in good yield.

Scheme 1$^a$

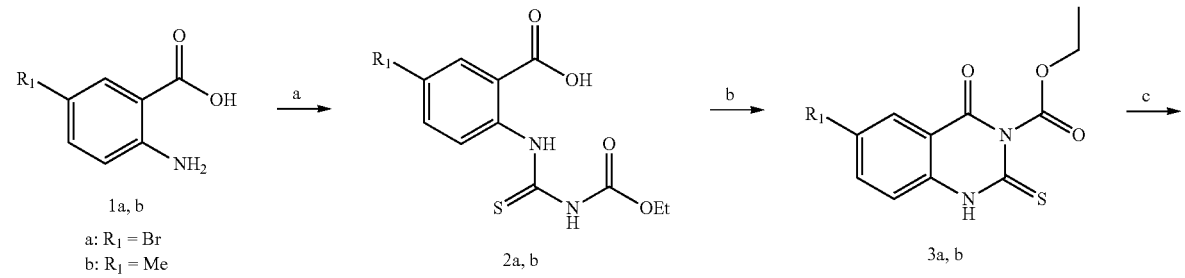

a: R$_1$ = Br
b: R$_1$ = Me

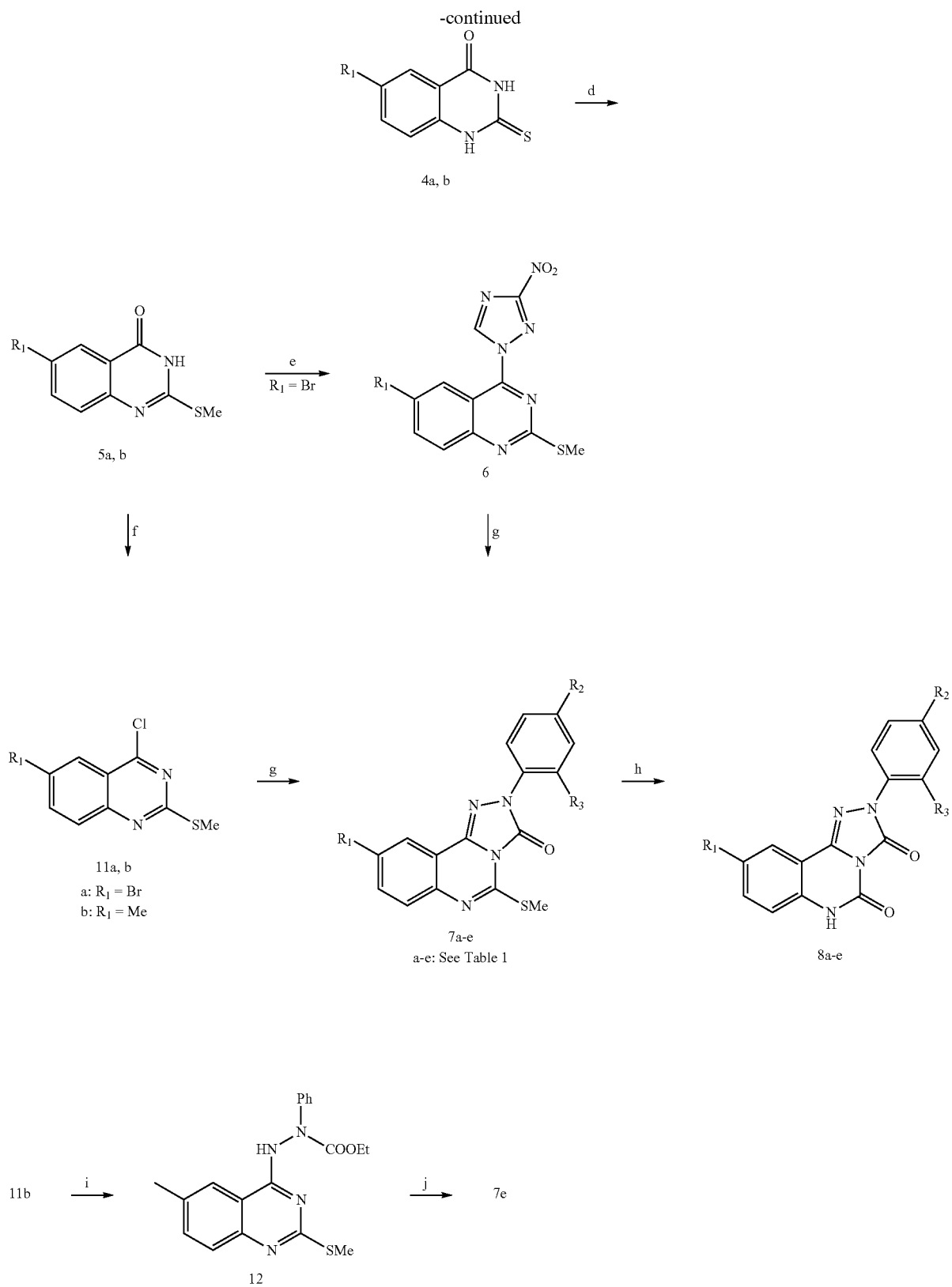
<sup>a</sup>Conditions: (a) Ethoxycarbonyl isothiocyanate, MeCN, 80° C., 4 h. (b) Ac₂O. 60° C., 1 h, (c) 0.5M NaOMe in MeOH, THF, reflux, 90 min. (d) DMF, 0.5M NaOMe in MeOH, then MeI, rt, 10 h, (e) 3-Nitro-1,2,4-triazole, Ph₃, I₂, toluene, DIPEA, 95° C., 1 h, (f) POCl₃, pyridine, 110° C., 18 h (g) DIPEA, 10a-d, 110° C., 60 h (h) m-CPBA (77%), CH₂Cl₂, rt, 6 h (i) DIPEA, 10a, 1,4-Dioxane, reflux, 48 h (j) LiOH, THF, rt, 2 h.

Scheme 2[a]
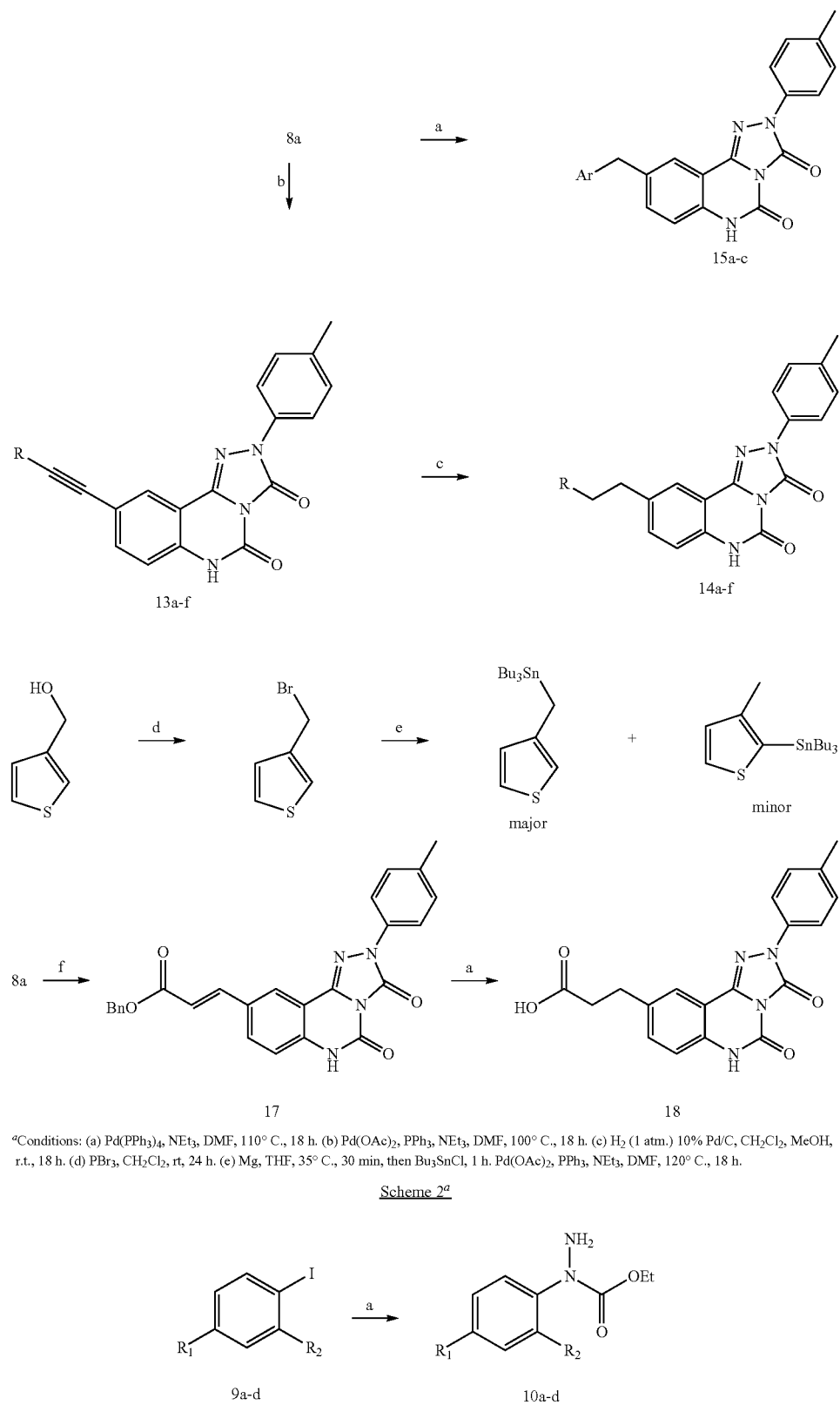
[a]Conditions: (a) Pd(PPh₃)₄, NEt₃, DMF, 110° C., 18 h. (b) Pd(OAc)₂, PPh₃, NEt₃, DMF, 100° C., 18 h. (c) H₂ (1 atm.) 10% Pd/C, CH₂Cl₂, MeOH, r.t., 18 h. (d) PBr₃, CH₂Cl₂, rt, 24 h. (e) Mg, THF, 35° C., 30 min, then Bu₃SnCl, 1 h. Pd(OAc)₂, PPh₃, NEt₃, DMF, 120° C., 18 h.
Scheme 2[a]
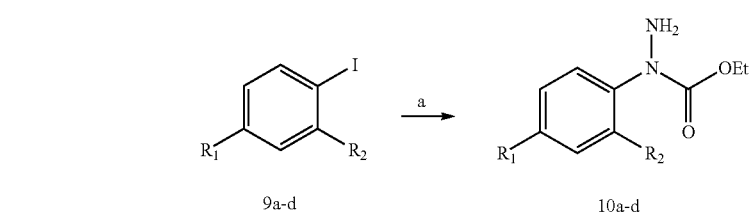
[a]Conditions: (a) CuI, 1,10-phenantrolein, ethyl carbazate, Cs₂CO₃, DMF, 80° C., 16 h.

Scheme 3[a]

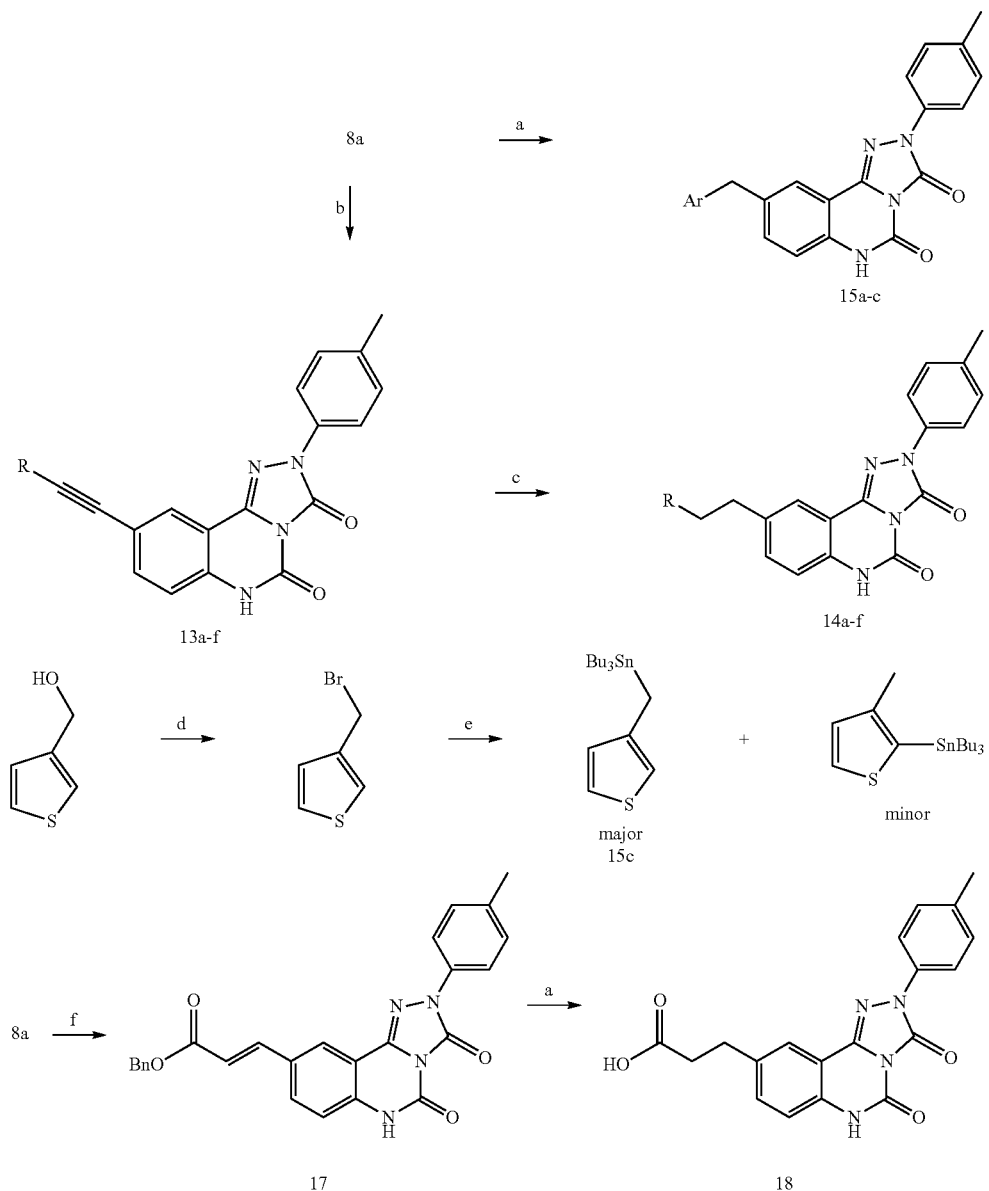

[a]Conditions: (a) Pd(PPh3)4, NEt3, DMF, 110° C., 18 h. (b) Pd(OAc)2, PPh3, NEt3, DMF, 100° C., 18 h. (c) H2 (1 atm.) 10% Pd/C, CH2Cl2, MeOH, r.t., 18 h. (d) PBr3, CH2Cl2, rt, 24 h (e) Mg, THF, 35° C., 30 min, then Bu3SnCl, 1 h. Pd(OAc)2, PPh3, NEt3, DMF, 120° C., 18 h.

Experimental Part

Reagents and solvents (except THF) were used froth commercial sources without purification. THF was distilled from sodium/benzophenone prior to use. $^1$H and $^{13}$C NMR were recorded at room temperature unless otherwise specified with a Bruker DR400 spectrometer at. The spectra were recorded in CDCl$_3$, DMSO-d$_6$, and C$_6$D$_6$, and the solvent signals (7.27 and 77.0, 2.50 and 39.5 or 7.18 and 128.06 ppm, respectively) were used as reference. Analytical thin layer chromatography (TLC) was performed on Kiselgel 60 F$_{254}$ plates (Merck). Column chromatography was performed on SiO$_2$ (Matrex LC-gel: 60A, 35-70 MY, Grace). Melting points (uncorrected) were determined with a Reichert microscope. ESI mass spectra were recorded with Micromass Q-TOF Micro.

5-Bromo-2-({[(ethoxycarbonyl)amino]carbonothioyl}amino)-benzoic acid (2a)

To a solution of 2-amino-5-bromobenzoic acid (8.09 g, 37.4 mmol) in 60 mL of dry MeCN was added ethoxycarbonyl isothiocyanate (4.32 mL, 37.4 mmol) and the mixture was stirred at reflux for 5 hours. Heating was removed and a white precipitate was filtered off, to give 2 as a white solid (12.3 g, 95%). mp: 180° C. (decomp.), $^1$H NMR (400 MHz, DMSO-d6) δ 11.38 (1H, s), 12.25 (1H, s), 8.07 (1H, d, J=8.8 Hz), 7.99 (1H, d, J=2.4 Hz), 7.78 (1H, dd, J=8.7 and J=2.4 Hz), 4.20 (2H, q, J=7.1 Hz), 1.25 (3H, t, J=7.1 Hz); $^{13}$C NMR (100 MHz, DMSO-d6) δ 179.2, 165.9, 152.9, 137.7, 134.5, 132.5, 129.5, 126.4, 117.9, 62.0, 14.1; HRMS (ESI): for $C_{11}H_{11}BrN_2O_4SNa$ calcd: 368.9521 [M+H]. found: 368.9523.

2-({[(Ethoxycarbonyl)amino]carbonothioyl}amino)-5-methylbenzoic acid (2b) was prepared and purified according to the procedure described for 2a, starting from 2-amino-5-methylbenzoic acid. The reaction yielded 2b (91%) as a white solid (mp: 197.0° C.).

$^1$H NMR (400 MHz, CDCl$_3$) δ 12.43 (1H, s), 8.3 (1H, s), 8.15 (1H, s), 7.91 (1H, d, J=1.8 Hz), 7.45 (1H, dd, J=8.38 and 1.8 Hz), 4.32 (2H, q, J=7.1 Hz), 2.41 (3H, s), 1.36 (3H, t, J=7.1 Hz); $^{13}$C NMR (400 MHz, CDCl$_3$) δ 178.4, 167.0, 152.0, 137.1, 136.3, 134.4, 131.9, 126.9, 121.3, 63.2, 21.1, 14.4; HRMS (ESI): for $C_{12}H_{15}N_2O_4S$ calcd: 283.0753 [M+H]. found 283.0758.

Ethyl 6-bromo-4-oxo-2-thioxo-1,4-dihydroquinazoline-3(2H)-carboxylate (3a)

Compound 2a (12.3 g, 35.5 mmol) was dissolved in 150 mL of acetic anhydride and stirred at 60° C. for 4 hour. The mixture was slowly cooled to 4° C. under crystallization and the white crystals formed were filtered off, washed with cold acetic anhydride and dried under vacuum, to give 3a (10.8 g, 32.8 mmol, 93%). mp: 214.0° C.

$^1$H NMR (400 MHz; DMSO-d6) δ 11.87 (1H, s), 8.06 (1H, d, J=2.4 Hz), 7.97 (1H, dd, J=8.7 and J=2.4 Hz), 7.47 (1H, d, J=8.7 Hz), 4.19 (2H, q, J=7.1 Hz); 1.25 (3H, t, J=7.1 Hz); $^{13}$C NMR (100 MHz, DMSO-d6) δ 183.4, 154.1, 153.3, 146.9, 138.8, 131.1, 126.3, 119.8, 118.9, 62.0, 14.2; HRMS (ESI): for $C_{11}H_9BrN_2O_3S$ calcd: 327.9517 [M+H]. found: 327.9524.

Ethyl 6-methyl-4-oxo-2-thioxo-1,4-dihydroquinazoline-3(2H)-carboxylate (3b) was prepared and purified according to the procedure described for 3a, starting from 2b. The reaction yielded 3b (100%) as a white solid (mp: 164.0° C.).

$^1$H NMR (400 MHz, CDCl$_3$) δ 8.57 (1H, bs), 7.95 (1H, s), 7.54 (1H, dd, J=8.3 and 2.0 Hz), 7.42 (1H, d, J=8.3 Hz), 4.30 (2H, q, J=7.1 Hz), 2.45 (3H, s), 1.34 (3H, t, J=7.1 Hz); $^{13}$C NMR (100 MHz, CDCl$_3$) δ 184.3, 152.8, 152.6, 145.7, 137.4, 137.2, 129.0, 124.8, 119.4, 62.9, 21.3, 14.4; HRMS (ESI): for $C_{12}H_{13}N_2O_3S$ calcd: 265.0647 [M+H]. found: 265.0647. Anal. Calcd. for $C_{12}H_{12}N_2O_3S$: C, 54.53; H, 4.58; N, 10.60. Found: C, 54.33; H, 4.62; N, 10.80.

6-Bromo-2-thioxo-2,3-dihydroquinazolin-4(1H)-one (4a)

A solution of sodium methoxide (0.5 M, 36.1 mmol) in methanol (72 mL) was added to a solution of 3a (10.8 g, 32.8 mmol) in 150 mL of dry THF and the mixture was heated at reflux for 90 min. The mixture was allowed to reach room temperature and quenched by addition of acetic acid (2.1 mL, 36.1 mmol). The mixture was concentrated under reduced pressure and 200 mL of ethyl alcohol and 100 mL of water was added and the mixture was heated at reflux for 30 min. The slurry was cooled to rt. and filtrated to give 4 white solid (8.43 g, 100%). mp: 350° C. (decomp.), $^1$H NMR (400 MHz, DMSO-d6) δ 12.67 (2H, bs), 7.97 (1H, d, J=2.3 Hz), 7.88 (1H, dd, J=8.7 and J=2.3 Hz), 7.29 (1H, d, J=8.7 Hz); $^{13}$C NMR (100 MHz, DMSO-d6) δ 174.4, 158.6, 139.8, 137.9, 128.7, 118.4, 118.1, 115.9; HRMS (FAB+): $C_8H_6ON_2BrS$ calcd; 256.9382 [M+H]. found 256.9382.

6-Methyl-2-thioxo-2,3-dihydroquinazolin-4(1H)-one (4b) was prepared and purified according to the procedure described for 4a, starting from 3b. The reaction yielded 4b (88%) as a white solid [mp: 312° C., (decomp.)];

$^1$H NMR (400 MHz, DMSO-d6) δ 12.65 (1H, s), 12.40 (1H, s), 7.75 (1H, s), 7.55 (1H, d, J=8.4 Hz), 7.27 (1H, d, J=8.4 Hz), 2.35 (3H, s); $^{13}$C NMR (100 MHz, DMSO-d6) δ 174.6, 160.5, 139.3, 137.3, 134.8, 127.0, 116.9, 116.7, 21.3; $C_9H_8ON_2S$ calcd; 192.0357 [M+H]. found 192.0354.

6-Bromo-2-(methylsulfanyl)quinazolin-4(3H)-one (5a)

To a solution of compound 4a (8.43 g, 32.8 mmol) in 130 mL of DMF was added a solution sodium methoxide (0.50 M, 32.8 mmol) in methanol (65.6 mL) and the mixture was stirred at room temperature for 15 minutes. Iodomethane (2.04 mL, 32.8 mmol) was added and the reaction mixture was stirred at room temperature for 22 hours. The solvents were evaporated under reduced pressure and the remaining solid was dissolved in 500 mL of EtOAc and washed with 400 mL of a saturated solution of aqueous NaHCO$_3$. The organic layer was dried over MgSO$_4$, concentrated under reduced pressure and precipitated from 50 mL of ethyl alcohol, to give 5a as a white solid (8.03 g, 90%). mp: 230° C., $^1$H NMR (400 MHz, DMSO-d6) δ 12.77 (1H, s), 8.09 (1H, J=2.4 Hz), 7.89 (1H, dd, J=8.7 and 2.4 Hz), 7.48 (1H, d, J=8.7 Hz), 2.57 (3H, s); $^{13}$C NMR (100 MHz, DMSO-d6) δ 160.0, 157.3, 147.4, 137.3, 128.3, 128.1, 121.5, 117.6, 12.8; HRMS (ESI): $C_9H_8N_2OSBr$ calcd: 270.9541 [M+H]. found 270.9539.

6-Methyl-2-(methylsulfanyl)quinazolin-4(3H)-one (5b) was prepared and purified according to the procedure described for 5a, starting from 4a. The reaction yielded 5b (77%) as a white solid (mp: 206.4° C.).

$^1$H NMR (400 MHz, CDCl$_3$) δ 10.63 (1H, s), 8.05 (1H, s), 7.55 (2H, m), 2.69 (3H, s), 2.47 (3H, s); $^{13}$C NMR (100 MHz, CDCl$_3$) δ 163.5, 154.4, 147.5, 136.5, 136.1, 126.39, 126.35, 119.7, 21.4, 13.6; HRMS (ESI): for $C_{10}H_{11}N_2OS$ calcd: 207.0592 [M+H]. found 207.0600.

6-Bromo-2-(methylsulfanyl)-4-(3-nitro-1H-1,2,4-triazol-1-yl)quinazoline (6)

Iodine (16.5 g, 65.1 mmol) was added to a suspension of compound 5a (8.03 g, 29.6 mmol), 3-nitro-1H-1,2,4-triazole (11.8 g, 103.6 mmol), triphenylphosphine (18.1 g, 69.1 mmol) in 630 mL of toluene. The reaction mixture was rapidly heated to 95° C. for 15 minutes after which 25 mL of N,N-diisopropylethylamine was added and the mixture was stirred for another 50 minutes. The reaction was cooled to room temperature and concentrated under reduced pressure. The crude product was precipitated from ethanol, to give 6 as a yellow solid (9.67 g, 89%). mp: 204° C., $^1$H NMR (400 MHz, DMSO-d6) δ 9.87 (1H, 4.8.97 (1H, dd, J=2.2 and 0.3 Hz), 8.18 dd, J=9.0 and 2.2 Hz), 7.88 (1H, dd, J=9.0 and 0.3 Hz), 2.70 (3H, s); $^{13}$C NMR (100 MHz, DMSO-d6) δ 167.0, 163.2, 152.3, 151.1, 148.2, 139.1, 129.1, 127.9; 120.5, 114.3, 14.0; HRMS (FAB+): $C_{11}H_8N_6O_2BrS$ calcd; 366.9613 [M+H]. found 366.9615.

9-Bromo-2-(4-methylphenyl)-5-(methylsulfanyl)[1,2,4]triazolo[4,3-c]quinazolin-3(2H)-one (7a)

N,N-Diisopropylethylamine (0.95 mL, 5.45 mmol) was added to a mixture of compound 6 (2.0 g, 5.447 mmol) and 10a (1.164 g, 5.99 mmol) and the reaction mixture were heated at 110° C. for 60 h. The mixture was cooled to rt., concentrated under reduced pressure and precipitated from ethanol to give 7a as a white solid (1.51 g, 69%). mp: 213° C., $^1$H NMR (400 MHz, DMSO-d6) δ 8.28 (1H, d, J=2.2 Hz), 7.94 (2H, dd, J=8.6 and 1.9 Hz), 7.70 (1H, dd, J=8.6 and J=2.2 Hz), 7.50 (1H, d, J=8.6 Hz), 7.28 (2H, d, J=8.6 Hz), 2.65 (3H, s), 2.40 (3H, s); $^{13}$C NMR (100 MHz, DMSO-d6) δ 150.9, 147.1, 141.7, 138.5, 136.5, 135.7, 134.9, 129.9, 129.9, 128.8, 125.3, 120.6, 119.5, 119.5, 116.1, 21.2, 13.6; HRMS (FAB+): $C_{17}H_{14}ON_4BrS$ calcd; 401.0072 [M+H]. found 401.0073.

9-Bromo-2-phenyl-5-(methylsulfanyl)[1,2,4]triazolo[4,3-c]quinazolin-3(2H)-one (7b) was prepared and purified according to the procedure described for 7a, starting from 10b. The reaction yielded 7b (76%) as a white solid (mp: 222° C.).

$^1$H NMR (400 MHz, CDCl$_3$) δ 8.26 (1H, d, J=1.6 Hz), 8.07 (2H, d, J=7.9 Hz), 7.69 (1H, dd, J=8.5 and J=1.6 Hz), 7.48 (3H, m), 7.30 (1H, t, J=7.4 Hz) 2.64 (3H, s); $^{13}$C NMR (100 MHz, DMSO-d6) δ 150.9, 147.1, 141.7, 138.6, 137.3, 135.8, 129.3, 129.3, 128.8, 126.6, 125.3, 120.7, 119.5, 119.5, 115.9, 13.6; HRMS (ESI): $C_{16}H_{12}ON_4BrS$ calcd; 386.9915 [M+H]. found 386.9912.

9-Bromo-2-(4-chlorophenyl)-5-(methylsulfanyl)[1,2,4]triazolo-c]quinazolin-3(2H)-one (7c) was prepared and purified according to the procedure described for 7a, starting from 10c. The reaction yielded 7c (70%) as a white solid (mp: 247° C.).

$^1$H NMR (400 MHz, CDCl$_3$) δ 8.27 (1H, d, J=2.2 Hz), 8.06 (2H, dt, J=9.0 and 2.0 Hz), 7.72 (1H, dd, J=8.7 and 2.2 Hz), 7.51 (1H, d, J=8.7 Hz), 7.44 (2H, dt, J=9.0 and 2.0 Hz), 2.65 (3H, s); $^{13}$C NMR (100 MHz, DMSO-d6) δ 150.8, 147.0, 141.8, 138.9, 136.0, 135.9, 132.0, 129.5, 129.5, 128.9, 125.4, 120.8, 120.6, 120.6, 115.8, 13.7; HRMS (ESI): $C_{16}H_{11}ON_4BrClS$ calcd: 420.9525 [M+H]. found 420.9525.

9-Bromo-2-(2-fluorophenyl)-5-(methylsulfanyl)[1,2,4]triazolo[4,3-c]quinazolin-3(2H)-one. (7d) was prepared and purified according to the procedure described for 7a, starting from 10d. The reaction yielded 7d (51%) as a white solid (mp: 256° C.).

$^1$H NMR (500 MHz, DMSO-d6) δ 8.11 (1H, d, J=2.1 Hz), 7.83 (1H, dd, J=8.7 and 2.1 Hz), 7.67 (1H, dt, J=7.7 and 1.2 Hz), 7.56 (2H, m), 7.43 (1H, t, J=9.6 Hz), 7.39 (1H, t, J=7.7 Hz), 2.64 (3H, s); $^{13}$C NMR (125 MHz, DMSO-d6) δ 155.9 (d, J=251.4 Hz), 150.5, 146.8, 140.9, 138.8, 135.1, 130.6 (d, J=7.9 Hz), 128.3, 127.9, 124.6 (d, J=3.7 Hz), 123.8, 123.3 6 (d, J=11.8 Hz), 119.1, 116.3 (d, J=19.3 Hz), 115.6, 12.3; HRMS (ESI): $C_{16}H_{11}ON_4BrFS$ calcd; 404.9821 [M+H]. found 404.9820.

9-Methyl-5-(methylthio)-2-phenyl[1,2,4]triazolo[4,3-c]quinazolin-3(2H)-one (7e)

A suspension of 12 (0.25 g, 0.68 mmol) and lithium hydroxide (0.057 g, 1.35 mmol) in 15 mL of dry THF was stirred at room temperature for 2 h. The mixture was poured onto 100 mL of a saturated solution of aqueous NaHCO$_3$ and extracted twice with 200 mL of EtOAc. The combined organic layers were dried over Na$_2$SO$_4$ and concentrated under reduced pressure to afford 7e as a white solid (0.17 g, 0.5 mmol, 78%). mp. >400° C.;

$^1$H NMR (400 MHz, CDCl$_3$) δ 8.09 (2H, dd, J=8.8 and 1.14 Hz), 7.49 (3H, m), 7.91 (1H, s), 7.41 (1H, dd, J=8.3 and 1.6 Hz), 7.29 (1H, t, J=7.4 Hz), 2.63 (3H, s), 2.46 (3H, s); $^{13}$C NMR (100 MHz, CDCl$_3$) δ 149.0, 147.3, 140.9, 139.9, 137.6, 137.5, 134.0, 129.2, 129.2, 126.9, 126.3, 122.3, 119.5, 119.5, 114.1, 21.5, 13.5; HRMS (ESI): for $C_{17}H_{15}N_4OS$ calcd: 323.0967 [M+H]. found 323.0962.

9-Bromo-2-(4-methylphenyl)-2,6-dihydro[1,2,4]triazolo[4,3-c]quinazoline-3,5-dione (8a)

To a solution of 7a (0.534 g, 1.33 mmol) in 60 mL of CH$_2$Cl$_2$ was added (77%) m-CPBA (0.597 g, 2.67 mmol) and mixture was stirred at room temperature for 6 h. A white precipitate was slowly formed. Saturated solutions of aqueous Na$_2$S$_2$O$_3$ (20 mL) and NaHCO$_3$ (20 mL) were subsequently added and the mixture was stirred vigorously for 30 min. The precipitate was filtered off, washed several times with water and heated in a mixture of 25 mL ethyl alcohol and 25 mL of water at reflux for 30 min. The mixture was cooled to rt. and filtered to give 8a as a white solid (0.488 g, 99%). mp: 369° C.;

$^1$H NMR (400 MHz, DMSO-d6) δ 11.52 (1H, s), 7.96 (1H, d, J=2.2 Hz), 7.86 (2H, d, J=8.4 Hz), 7.58 (1H, dd, J=8.8 and 2.2 Hz), 7.30 (2H, d, J=8.4 Hz), 7.02 (1H, d, J=8.8 Hz), 2.33 (3H, s); $^{13}$C, NMR (100 MHz, DMSO-d6) δ 146.6, 143.7, 139.4, 136.6 135.2, 135.1, 134.7, 129.6, 129.6, 124.5, 118.9, 117.9, 117.9, 114.9, 111.3, 20.5; HRMS (ESI): $C_{16}H_{11}N_4O_2Br$ calcd: 371.0144 [M+H]. found 371.0143. Anal. Calcd. for $C_{16}H_{11}N_4O_2Br$: C, 51.77; H, 2.99; N, 15.09. Found: C, 51.87; H, 2.87; N, 15.02.

9-Bromo-2-phenyl-2,6-dihydro[1,2,4]triazolo[4,3-c]quinazoline-3,5-dione (8b) was prepared and purified according to the procedure described for 8a, starting from 7b. The reaction yielded 8b (100%) as a white solid (mp: 405° C.).

$^1$H NMR (400 MHz, DMSO-d6) δ 11.55 (1H, s), 8.06 (1H, d, J=2.2 Hz), 7.97 (2H, d, J=7.7 Hz), 7.73 (1H, dd, J=8.7 and 2.2 Hz), 7.52 (1H, t, J=8.0 Hz), 7.34 (2H, t, J=7.4 Hz), 7.13 (1H, d, J=8.7 Hz); $^{13}$C NMR (100 MHz, DMSO-d6) δ 146.6, 143.6, 139.6, 137.1, 136.6, 135.2, 129.2, 129.2, 125.8, 124.6, 118.8, 118.8, 117.9, 114.9, 111.2; HRMS (ESI): $C_{15}H_{10}N_4O_2Br$ calcd: 356.9987 [M+H]. found 356.9993. Anal. Calcd, for $C_{15}H_9N_4O_2Br$: C, 50.44; H, 2.54; N, 15.69. Found: C, 50.14; H, 2.69; N, 15.61.

9-Bromo-2-(4-chlorophenyl)-2,6-dihydro[1,2,4]triazolo[4,3-c]quinazoline-3,5-dione (8c) was prepared and purified according to the procedure described for 8a, starting from 7c. The reaction yielded 8c (100%) as a white solid [mp: 387° C. (decomp.)].

$^1$H NMR (400 MHz, DMSO-d6) δ 8.07 (1H, bs), 8.02 (2H, d, J=7.4 Hz), 7.74 (1H, bd, J=7.8 Hz), 7.59 (2H, d, J=7.4 Hz), 7.13 (1H, d, J=7.8 Hz); $^{13}$C NMR (100 MHz, DMSO-d6) δ 146.6, 143.6, 139.9, 136.8, 136.0, 135.3, 129.7, 129.2, 129.2, 124.7, 120.2, 120.2, 118.1, 114.9, 111.1; HRMS (ESI): $C_{15}H_9N_4O_2BrCl$ calcd: 390.9597 [M+H]. found 390.9599. Anal. Calcd. for $C_{15}H_8N_4O_2BrCl$: C, 46.01; H, 2.06; N, 14.31. Found: C, 46.30; H, 2.09; N, 14.14.

9-Bromo-2-(2-fluorophenyl)-2,6-dihydro[1,2,4]triazolo[4,3-c]quinazoline-3,5-dione (8d) was prepared and purified according to the procedure described for 8a, starting from 7d. The reaction yielded 8d (100%) as a white solid [mp: 347° C. (decomp.)].

$^1$H NMR (400 MHz, DMSO-d6) δ 7.89 (1H, s), 7.63 (2H, m), 7.54 (1H, m), 7.47 (1H, t, J=8.7 Hz), 7.38 (1H, t, J=8.7 Hz), 7.07 (2H, d, J=8.7 Hz); $^{13}$C NMR (100 MHz, DMSO-d6) δ 156.3 (d, J=250.6 Hz), 147.8, 145.3, 141.7, 141.1, 134.7, 130.7 (d, J=7.8 Hz), 128.5, 125.0 (d, J=3.5 Hz), 124.1, 123.9 (d, J=11.7 Hz), 120.6, 116.7 (d, J=19.1 Hz), 113.0, 111.5; HRMS (ESI): $C_{15}H_9N_4O_2BrF$ calcd: 374.9893 [M+H]. found 374.9889. Anal. Calcd. for $C_{15}H_8N_4O_2BrF$: C, 48.02; H, 2.15; N, 14.93; 0, 8.53. Found: C, 48.20; H, 2.05; N, 15.09.

9-Methyl-2-phenyl-2,6-dihydro[1,2,4]triazolo[4,3-c]quinazoline-3,5-dione (8e) was prepared and purified according to the procedure described for 8a, starting from 7e. The reaction yielded 8e (100%) as a white solid [mp. 330° C. (decomp.)];

$^1$H NMR (500 MHz, DMSO-d6, 323K) □ 7.96 (1H, d, J=7.7 Hz), 7.77 (1H, s), 7.50 (2H, t, J=7.7 Hz), 7.35 (3H, m), 7.21 (1H, d, J=8.36 Hz), 2.33 (3H, s); $^{13}$C NMR (125 MHz, DMSO-d6, 323K) □ 146.5, 143.3, 140.3, 136.9, 135.0, 133.0, 132.4, 128.6, 128.6, 125.3, 121.7, 118.7, 118.7, 115.5, 108.6, 19.8; HRMS (ESI): for $C_{16}H_{13}N_4O_2$ calcd: 293.1039 [M+H]. found 293.1033. Anal. Calcd. for $C_{16}H_{12}N_4O_2$: C, 65.75; H, 4.14; N, 19.17; O, 10.95. Found: C, 65.73; H, 4.10; N, 19.30.

Ethyl 1-(4-methylphenyl)hydrazinecarboxylate 10a

N,N-Dimethylformamide (20 mL) was added to a mixture of 4-iodotoluene (3.0 g, 13.8 mmol), ethyl carbonate (1.72 g, 16.5 mmol), 1,10-phenanthroline (0.50 g, 2.76 mmol), copper(I) iodine (0.131 g, 0.69 mmol) and cesium carbonate (6.3 g, 19.3 mmol) and the mixture was heated under $N_2$ at 80° C. for 18 h. The crude mixture was concentrated in vacuo and purified by chromatography on a silica gel column. Elution with n-heptane/EtOAc (4:1) as eluent afforded 10a as a white solid (2.22 g, 83%). mp. 35° C., $^1$H NMR (400 MHz, $C_6D_6$) δ 7.53 (2H, d, J=8.3 Hz), 6.98 (2H, d, J=8.3 Hz), 4.00 (2H, q, J=7.1 Hz), 3.96 (2H, bs), 2.08 (3H, s), 0.94 (3H, t, J=7.1 Hz), $^{13}$C NMR (100 MHz, $C_6D_6$) δ 155.9, 141.2, 134.0, 129.0, 129.0, 123.4, 123.4, 62.1, 20.8, 14.6; HRMS (ESI): $C_{10}H_{15}N_2O_2$ calcd: 195.1134 [M+H]. found 195.1129.

Ethyl 1-phenylhydrazinecarboxylate 10b was prepared and purified according to the procedure described for 10a, starting from iodobenzene. The reaction yielded 10b (76%) as a white solid (mp: 25° C.).

$^1$H NMR (400 MHz, $C_6D_6$) δ 7.66 (2H, bd, J=7.55 Hz), 7.18 (2H, m), 6.94 (1H, tt, J=7.4 and 1.1 Hz), 3.99 (2H, q, J=7.1 Hz), 3.93 (2H, bs), 0.95 (3H, t, J=7.1 Hz); $^{13}$C NMR (100 MHz, $C_6D_6$) δ 155.8, 143.6, 128.4, 124.5, 124.5, 123.2, 123.2, 62.2, 14.5; HRMS (ESI): $C_9H_{13}N_2O_2$ calcd: 181.0977 [M+H]. found 181.0980.

Ethyl 1-(4-chlorophenyl)-hydrazinecarboxylate (10c) was prepared and purified according to the procedure described for 10a, starting from 1-chloro-4-iodobenzene. The reaction yielded 10c (40%) as a white semisolid.

$^1$H NMR (400 MHz, $C_6D_6$) δ 7.43 (2H, d, J=7.0 Hz), 7.11 (2H, dt, J=7.0 and 2.2 Hz), 3.92 (2H, q, J=7.1 Hz), 3.79 (2H, bs), 0.91 (3H, t, J=7.1 Hz); $^{13}$C NMR (100 MHz, $C_6D_6$) δ 155.3, 142.1, 129.5, 128.4, 128.4, 124.0, 124.0; 62.3, 14.5; HRMS (ESI): $C_9H_{12}N_2O_2Cl$ calcd: 215.0587 [M+H]. found 215.0586.

Ethyl 1-(2-fluorophenyl)-hydrazinecarboxylate (10d) was prepared and purified according to the procedure described for 10a, starting from 1-fluoro-2-iodobenzene. The reaction yielded 10d (22%) as a white semisolid.

$^1$H NMR (400 MHz, $C_6D_6$) δ 7.22 (1H, m), 6.80-6.91 (3H, m). 4.27 (2H, bs), 4.11 (2H, q, J=7.1 Hz), 1.12 (3H, t, J=7.1 Hz); $^{13}$C NMR (100 MHz, $C_6D_6$) δ 157.9 (d, J=248 Hz), 156.8, 131.8 (d, J=12 Hz), 128.8, 128.0 (d, J=23.6 Hz), 124.1 (d, J=3.8 Hz), 116.2 (d, J=20.3 Hz), 62.5, 14.5; HRMS (ESI): $C_9H_{12}N_2O_2F$ calcd: 199.0885 [M+H]. found 199.0888.

6-Bromo-4-chloro-2-(methylsulfanyl)quinazoline (11a)

To a suspension of compound 5a (0.65 g, 2.4 mmol) in 6.2 mL of $POCl_3$ was added 10 μL of pyridine and the mixture was heated at 110° C. for 18 hours. The reaction mixture was cooled to rt. and concentrated under reduced pressure. A saturated solution of 50 mL of aqueous $NaHCO_3$ was added to the crude solid and the mixture was extracted with 50 mL of EtOAc. The organic layer was dried over $MgSO_4$, concentrated under reduced pressure and purified by chromatography on a silica gel column. Elution with n-heptane/EtOAc (4:1) as eluent afforded 11a as a white solid (0.52 g, 75%). mp: 124° C., $^1$H NMR (400 MHz, DMSO-d6) δ 8.29 (1H, J=2.2 Hz), 7.92 (1H, dd, J=8.9 and J=2.2 Hz), 7.73 (1H, J=8.9 Hz), 2.66 (3H, s); $^{13}$C NMR (100 MHz, DMSO-d6) δ 168.5, 160.7, 150.6, 138.9, 129.0, 128.4, 122.2, 120.7, 14.6; HRMS (FAB+): $C_9H_7N_2ClBrS$ calcd: 288.9202 [M+H]. found 288.9200.

4-Chloro-6-methyl-2-(methylsulfanyl)quinazoline (11b) was prepared and purified according to the procedure described for 11a, starting from 5b. The reaction yielded 11b (77%) as a white solid (mp: 204.7° C., decomp).

$^1$H NMR (400 MHz, $CDCl_3$) δ 7.86 (1H, s), 7.73 (1H, d, J=8.6 Hz), 7.66 (1H, d, J=8.6 Hz), 2.65 (3H, s), 2.55 (3H, s); $^{13}$C NMR (100 MHz, $CDCl_3$) δ 166.7, 161.2, 150.6, 137.5, 137.5, 127.0, 124.9, 121.0, 21.8, 14.5; HRMS (ESI): for $C_{10}H_{10}N_2SCl$ calcd: 225.0253 [M+H]. found 225.0256.

Ethyl 2-[6-methyl-2-(methylthio)quinazolin-4(3H)-ylidene]-1-phenylhydrazinecarboxylate (12)

N,N-Diisopropylethylamine (0.104 mL, 0.6 mmol) was added to a solution of 11b (0.071 g, 0.3 mmol) and 10a, (0.057 g, 0.3 mmol) in 5 mL of dioxane and the solution was heated at reflux for 48 h; during which a white precipitate fell out. The white slurry was filtered and the precipitate was washed with dioxane to give 12 as a white solid. (0.110 g, 100%). mp. 229.7° C.;

$^1$H NMR (500 MHz, DMSO-d6, 323K) δ 8.48 (1H, s), 7.78 (2H, s), 7.59 (2H, d, J=7.8 Hz), 7.37 (2H, t, J=7.7 Hz), 7.22 (1H, t, J=7.4 Hz), 4.19 (2H, q, J=7.1 Hz), 2.56 (3H, s), 2.46 (3H, s), 1.13 (3H, t, J=7.1 Hz); $^{13}$C NMR (125 MHz, DMSO-d6, 323K) δ 165.2, 158.3, 153.1, 141.6, 140.8, 136.8, 136.2, 128.2, 125.6, 123.3, 122.8, 120.5, 109.7, 62.0, 20.6, 13.9, 13.1; HRMS (ESI): for $C_{19}H_{21}N_4O_2S$ calcd: 369.1385 [M+H]. found 369.1380.

2-(4-Methylphenyl)-9-phenylethynyl-2,6-dihydro[1,2,4]triazolo[4,3-c]-quinazoline-3,5-dione (13a)

To a stirred solution of phenylacetylene (15.0 μg, 0.137 mmol) and 8a (25.3 mg, 0.0682 mmol) in a mixture of 2 mL of DMF and 1 mL of $NEt_3$, was added $Pd(OAc)_2$ (1.53 mg, 6.82 μmol) and triphenylphosphine (3.57 mg, 13.6 μmol) in a seal tube. The tube was sealed under argon and the mixture was stirred at 100° C. for 18 h. The mixture was cooled and concentrated to dryness in vacuo and the crude product was purified by chromatography on a silica gel column. Elution with n-heptane/EtOAc (2:1) as eluent yielded 13a as a white solid (14 mg, 70%). mp: >300° C. (decomp.), $^1$H NMR (400 MHz, DMSO-d6) δ 11.61 (1H, s), 8.06 (1H, d, J=1.9 Hz), 7.85 (2H, d, J=8.5 Hz), 7.70 (1H, dd, J=8.6 and 1.9 Hz), 7.58 (2H, m), 7.44 (3H, m), 7.31 (2H, d, J=8.5 Hz), 7.20 (1H, d, J=8.6 Hz), 2.34 (3H, s); $^{13}$C NMR (100 MHz, DMSO-d6) δ 146.5, 143.7, 139.7, 137.2, 135.1, 134.7, 131.4, 131.4, 129.5, 129.5, 128.9, 128.8, 128.8, 125.2, 122.0, 118.8, 118.8, 117.0, 116.3, 109.8, 89.5, 88.1, 20.5; HRMS (ESI): for $C_{24}H_{17}N_4O_2$ calcd: 393.1352 [M+H]. found: 393.1350. Anal. Calcd. for $C_{24}H_{16}N_4O_2$: C, 73.46; H, 4.11; N, 14.28. Found: C, 73.26; H, 4.19; N, 14.07.

2-(4-Methylphenyl)-9-(3-thienylethynyl)-2,6-dihydro[1,2,4]triazolo[4,3-c]-quinazoline-3,5-dione (13b) was prepared and purified according to the procedure described for 13a, starting from 3-ethynylthiophene and 8a. The reaction yielded 13b (40%) as a white solid (mp: >320° C., decomp).

$^1$H NMR (400 MHz, DMSO-d6) δ 11.60 (1H, s), 8.06 (1H, d, J=1.8 Hz), 7.93 (1H, dd, J=2.9 and 1.2 Hz), 7.87 (2H, d, J=8.4 Hz), 7.67 (2H, m), 7.34 (2H, d, J=8.4 Hz), 7.30 (1H, dd, J=5.0 and 1.2 Hz), 7.21 (1H, d, J=8.5 Hz), 2.35 (3H, s); $^{13}$C NMR (100 MHz, DMSO-d6) δ 146.6, 143.7, 139.7, 137.2, 135.1, 134.9, 134.8, 130.2, 129.6, 129.6, 129.6, 127.0, 125.0, 120.9, 118.8, 118.8, 117.1, 116.3, 109.8, 87.4, 85.1, 20.5; HRMS (ESI): for $C_{22}H_{15}N_4O_2S$ calcd: 399.0916 [M+H]. found: 399.0920.

2-(4-Methylphenyl)-9-(pyridin-2-ylethynyl)-2,6-dihydro[1,2,4]triazolo[4,3-c]-quinazoline-3,5-dione (13c) was prepared and purified according to the procedure described for 13a, starting from 2-ethynylpyridine and 8a. The reaction yielded 13c (75%) as a white solid (mp: 330° C.).

$^1$H NMR (400 MHz, DMSO-d6) δ 11.65 (1H, s), 8.63 (1H, ddd, J=4.9, 1.8 and 1.0 Hz), 8.14 (1H, bd, J=1.9 Hz), 7.86 (3H, m), 7.77 (1H, dd, J=8.5 and 1.9 Hz), 7.69 (1H, dt, J=7.8 and 1.0 Hz), 7.43 (1H, ddd, J=7.6, 4.9 and 1.2 Hz), 7.33 (2H, d, J=8.4 Hz), 7.24 (1H, d, J=8.5 Hz), 2.34 (3H, s); $^{13}$C NMR (100 MHz, DMSO-d6) δ 150.2, 146.6, 143.7, 142.1, 139.7, 137.8, 136.8, 135.4, 135.1, 134.8, 129.6, 129.6, 127.4, 125.7, 125.7, 123.6, 118.8, 116.4, 116.1, 109.9, 89.2, 87.2, 20.5; HRMS (ESI): for $C_{23}H_{16}N_5O_2$ calcd: 394.1304 [M+H]. found: 394.1310.

2-(4-Methylphenyl)-9-(pyridin-3-ylethynyl)-2,6-dihydro[1,2,4]triazolo[4,3-c]-quinazoline-3,5-dione (13d) was prepared and purified according to the procedure described for 13a, starting from 3-ethynylpyridine and 8a. The reaction yielded 13d (50%) as a white solid (mp: 339° C.).

$^1$H NMR (400 MHz, DMSO-d6) δ 11.62 (1H, s), 8.76 (1H, bs), 8.59 (1H, dd, J=4.9 and 1.5 Hz), 8.06 (1H, d, J=1.7 Hz), 7.97 (1H, dt, J=7.8 and 1.5 Hz), 7.83 (2H, d, J=8.4 Hz), 7.69 (1H, dd, J=8.5 and 1.7 Hz), 7.46 (1H, dd, J=7.8 and 4.9 Hz), 7.29 (2H, d, J=8.4 Hz), 7.19 (1H, d, 8.5), 2.32 (3H, s); $^{13}$C NMR (100 MHz, DMSO-d6) δ 151.7, 149.0, 146.4, 143.6, 139.6, 139.6, 138.5, 137.5, 135.1, 134.7, 129.5, 129.5, 125.4, 123.6, 119.2, 118.7, 118.7, 116.4, 116.3, 109.7, 91.1, 86.4, 20.5; HRMS (ESI): for $C_{23}H_{16}N_5O_2$ calcd: 394.1304 [M+H]. found: 394.1305.

2-(4-Methylphenyl)-9-(pyridin-4-ylethynyl)-2,6-dihydro[1,2,4]triazolo[4,3-c]-quinazoline-3,5-dione (13e) was prepared, and purified according to the procedure described for 13a, starting from 4-ethynylpyridine hydrochloride and 8a. The reaction yielded 13e (39%) as a white solid (mp: 330° C.).

$^1$H NMR (400 MHz, DMSO-d6) δ 11.66 (1H, s), 8.63 (2H; d, J=5.9 Hz), 8.15 (1H, d, J=1.7 Hz), 7.85 (2H, d, J=8.4 Hz), 7.76 (1H, dd, J=8.5 and 1.8 Hz), 7.55 (2H, d, J=5.9 Hz), 7.32 (2H, d, J=8.4 Hz), 7.23 (1H, d, J=8.5 Hz), 2.34 (3H, s); $^{13}$C NMR (100 MHz, DMSO-d6) 149.9, 149.9, 146.5, 143.6, 139.6, 137.9, 135.3, 135.1, 134.7, 130.0, 129.5, 129.5, 125.8, 125.3, 125.3, 118.7, 118.7, 116.4, 115.9, 109.9, 92.4, 86.9, 20.5; HRMS (ESI): for HRMS (ESI): for $C_{23}H_{16}N_5O_2$ calcd: 394.1304 [M+H]. found: 394.1298.

2-(4-Methylphenyl)-9-[(4-phenoxyphenyl)ethynyl]-2,6-dihydro[1,2,4]triazolo[4,3-c]-quinazoline-3,5-dione (13f) was prepared and purified according to the procedure described for 13a, starting from 1-ethynyl-4-phenoxybenzene and 8a. The reaction yielded 13f (60%) as a white solid (mp: 216° C.).

$^1$H NMR (400 MHz, DMSO-d6) δ 11.60 (1H, s), 8.06 (1H, d, J=1.9 Hz), 7.85 (2H, d, J=8.5 Hz), 7.69 (1H, dd, J=8.5 and 1.9 Hz), 7.59 (2H, dt, J=8.8 and 1.9 Hz), 7.44 (2H, m), 7.32 (2H, d, J=8.3 Hz), 7.20 (2H, m), 7.09 (2H, dd, J=8.7 and 1.1 Hz), 7.02 (2H, dt, J=8.8 and 1.9 Hz), 2.34 (3H, s); $^{13}$C NMR (100 MHz, DMSO-d6) δ 157.5, 155.6, 146.6, 143.7, 139.8, 137.1, 135.1, 135.0, 134.8, 133.4, 133.4, 130.3, 130.3, 129.6, 129.6, 125.1, 124.3, 119.5, 119.5, 118.8, 118.8, 118.2, 117.2, 116.6, 116.3, 109.8, 89.2, 87.5, 20.5; HRMS (ESI): for $C_{30}H_{21}N_4O_3$ calcd: 485.1614 [M+H]. found: 485.1614.

9-(Biphen-4-ylethynyl)-2-(4-methylphenyl)-2,6-dihydro[1,2,4]triazolo[4,3-c]-quinazoline-3,5-dione (13g) was prepared and purified according to the procedure described for 13a, starting from 4-ethynylbiphenyl and 8a. The reaction yielded 13g (69%) as a white solid (mp: >350° C., decomp.).

$^1$H NMR (400 MHz, DMSO-d6, 373K) δ 11.30 (1H, s), 8.12 (1H, bs), 7.86 (2H, d, J=8.2 Hz), 7.72 (5H, m), 7.67 (2H, dt, J=8.2 Hz), 7.49 (2H, t, J=7.6 Hz), 7.40 (1H, d, J=7.4 Hz), 7.33 (2H, d, J=8.1 Hz), 7.28 (2H, d, J=8.5 Hz), 2.38 (3H, s); $^{13}$C NMR (100 MHz, DMSO-d6, 373K) δ 146.1, 143.0, 140.1, 139.2, 138.8, 136.9, 134.8, 134.5, 134.4, 131.4, 131.4, 128.9, 128.9, 128.4, 128.4, 127.2, 126.3, 126.3, 126.1, 126.1, 124.7, 120.8, 118.8, 118.8, 117.0, 115.9, 109.3, 89.1, 88.4, 19.8; HRMS (ESI): for $C_{30}H_{21}N_4O_2$ calcd: 469.1665 [M+H]. found: 469.1665.

9-(3-Hydroxyphenyl)ethynyl-2-(4-methylphenyl)-2,6-dihydro[1,2,4]triazolo[4,3-c]-quinazoline-3,5-dione (13i) was prepared and purified according to the procedure described for 13a, starting from 3-tert-butyldimethylsilyloxy-phenylacetylene and 8a. The reaction yielded 13i (32%) as a white solid [mp: 300° C. (decomp.)].

$^1$H NMR (400 MHz, DMSO-$d_6$) δ 11.60 (1H, s), 9.72 (1H, s), 8.05 (1H, s), 7.86 (2H, d, J=8.0 Hz), 7.70 (1H, d, J=8.3 Hz), 7.32 (2H, d, J=8.0 Hz), 7.22 (2H, m), 7.00 (1H, d, J=7.5 Hz), 6.93 (1H, s); 6.84 (1H, d, J=7.8 Hz), 2.34 (3H, s); $^{13}$C NMR (100 MHz, DMSO-$d_6$) δ 157.4, 146.6, 143.7, 139.7, 137.2, 135.1, 135.1, 134.8, 129.9, 129.5, 129.5, 125.2, 122.9, 122.3, 118.8, 118.8, 117.8, 117.1, 116.4, 116.3, 109.8, 20.5; HRMS (ESI): for $C_{24}H_{17}N_4O_3$ calcd: 409.1301 [M+H]. found: 409.1299.

2-(4-Methylphenyl)-9-(2-phenylethyl)-2,6-dihydro[1,2,4]triazolo[4,3-c]-quinazoline-3,5-dione (14a)

A catalytic amount of 10% Pd/C and 13a (20.0 mg, 0.0510 mmol) in a mixture of 2 mL of dichloromethane and 2 mL of methyl alcohol was stirred during 12 h under $H_2$ at atmospheric pressure. The mixture was filtered through celite, washed with additionally methyl alcohol and triturated from ethyl alcohol to afford 14a (16 mg, 0.0404 mmol, 79%) as a white solid. mp: 303° C.;

$^1$H NMR (400 MHz, DMSO-d6) δ 11.34 (1H, s), 7.85 (2H, d, J=8.4 Hz), 7.83 (1H, d, J=1.7 Hz), 7.43 (1H, dd, J=8.4 and 1.7 Hz), 7.33 (2H, d, J=8.4 Hz), 7.27 (3H, m), 7.18 (1H, m), 7.10 (1H, d, J=8.4 Hz), 2.92 (4H, m), 2.35 (3H, s); $^{13}$C NMR (100 MHz, DMSO-d6) δ 146.7, 143.9, 141.2, 140.5, 136.9, 135.4, 135.0, 134.8, 133.0, 129.5, 129.5, 128.4, 128.4, 128.2, 128.2, 125.9, 121.9, 118.8, 118.8, 115.6, 109.0, 37.0, 36.2, 20.5; HRMS (ESI): for $C_{24}H_{21}N_4O_2$ calcd: 397.1665 [M+H]. found: 397.1669. Anal. Calcd. for $C_{24}H_{20}N_4O_2$: C, 72.71; H, 5.08; N, 14.13. Found: C, 72.46; H, 4.99; N, 14.07.

2-(4-Methylphenyl)-9-[2-(3-thienyl)ethyl]-2,6-dihydro[1,2,4]triazolo[4,3-c]-quinazoline-3,5-dione (14b) was prepared and purified according to the procedure described for 14a, starting from 13b. The reaction yielded 14b (88%) as a white solid (mp: 281° C.).

$^1$H NMR (400 MHz, DMSO-d6) δ 11.40 (1H, s), 7.85 (3H, m), 7.44 (2H, m), 7.32 (2H, d, J=7.9 Hz), 7.18 (1H, s), 7.12 (1H, d, J=8.3 Hz), 7.05 (1H, d, J=4.34 Hz); $^{13}$C NMR (100

MHz, DMSO-d6) δ 146.7, 143.9, 141.6, 140.5, 136.9, 135.4, 135.0, 134.8, 132.9, 129.5, 129.5, 128.4, 125.8, 121.8, 120.8, 118.8, 118.8, 115.6, 109.0, 35.3, 31.4, 20.5; HRMS (ESI): for $C_{22}H_{19}N_4O_2S$ calcd: 403.1229 [M+H]. found: 402.1226. Anal. Calcd. for $C_{22}H_{19}N_4O_2S$: C, 65.65; H, 4.51; N, 13.92. Found: C, 72.46; H, 4.99; N, 14.07.

2-(4-Methylphenyl)-9-[2-(2-pyridyl)ethyl]-2,6-dihydro [1,2,4]triazolo[4,3-c]-quinazoline-3,5-dione (14c) was prepared and purified according to the procedure described for 14a, starting from 13c. The reaction yielded 14c (85%) as a white solid (mp: >300° C., decomp.).

$^1$H NMR (400 MHz, DMSO-d6) δ 11.39 (1H, s), 8.58 (1H, d, J=4.42 Hz), 7.84 (4H, m), 7.43 (2H, m), 7.34 (3H, m), 7.11 (1H, d, J=8.4 Hz), 3.10 (4H, m) 2.34 (3H, s); $^{13}$C NMR (100 MHz, DMSO-d6) δ 159.4, 147.4, 146.7, 143.8, 140.4, 138.5, 136.5, 135.5, 135.0, 134.8, 132.9, 129.5, 129.5, 123.8, 122.1, 121.9, 118.8, 118.8, 115.7, 109.1, 39.1, 34.0, 20.5; HRMS (ESI): for $C_{23}H_{20}N_5O_2$ calcd: 398.1617 [M+H]. found: 398.1621. Anal. Calcd. for $C_{23}H_{19}N_5O_2$: C, 65.51; H, 4.82; N, 17.62. Found: C, 65.35; H, 4.71; N, 17.78.

2-(4-Methylphenyl)-9-[2-(3-pyridyl)ethyl]-2,6-dihydro [1,2,4]triazolo[4,3-c]-quinazoline-3,5-dione (14d) was prepared and purified according to the procedure described for 14a, starting from 13d. The reaction yielded 14d (91%) as a white solid (mp: 292° C.).

$^1$H NMR (400 MHz, DMSO-d6) δ 11.40 (1H, s), 8.57 (1H, s), 8.50 (1H, bs), 7.91 (1H, d, J=7.8 Hz), 7.82 (3H, m), 7.50 (1H, dd, J=7.8 and 5.00 Hz), 7.41 (1H, dd, J=8.4 and 1.7 Hz), 7.30 (2H, d, J=8.4 Hz), 7.11 (1H, d, J=8.4 Hz), 2.97 (4H, m), 2.32 (3H, s); $^{13}$C NMR (100 MHz, DMSO-d6) δ 147.3, 146.7, 145.0, 143.8, 140.4, 138.9, 137.9, 136.2, 135.5, 135.0, 134.8, 132.9, 129.5, 129.5, 124.4, 121.9, 118.8, 118.8, 115.7, 109.0, 35.5, 33.7, 20.5; HRMS (ESI): for $C_{23}H_{20}N_5O_2$ calcd: 398.1617 [M+H]. found: 398.1620. Anal. Calcd. for $C_{23}H_{19}N_5O_2$: C, 65.51; H, 4.82; N, 17.62. Found: C, 65.59; H, 4.89; N, 17.53.

2-(4-Methylphenyl)-9-[2-(4-pyridyl)ethyl]-2,6-dihydro [1,2,4]triazolo[4,3-c]-quinazoline-3,5-dione (14e) was prepared and purified according to the procedure described for 14a, starting from 13e. The reaction yielded 14e (91%) as a white solid (mp: 294° C.).

$^1$H NMR (400 MHz, DMSO-d6) δ 11.37 (1H, s), 8.47 (1H, d, J=6.0 Hz), 7.85 (3H, m), 7.45 (1H, dd, J=8.4 and 1.9 Hz), 7.34 (4H, m), 7.11 (1H, d, J=8.4 Hz), 2.97 (4H, m), 2.35 (3H, s); $^{13}$C NMR (100 MHz, DMSO-d6) δ 151.0, 148.8, 148.8, 146.7, 143.8, 140.4, 136.2, 135.5, 135.0, 134.8, 132.9, 129.5, 129.5, 124.3, 124.3, 121.8, 118.8, 118.8, 115.7, 109.0, 36.0, 34.8, 20.5; HRMS (ESI): for $C_{23}H_{20}N_5O_2$ calcd: 398.1617 [M+H]. found: 398.1615. Anal. Calcd. for $C_{23}H_{19}N_5O_2$: C, 65.51; H, 4.82; N, 17.62. Found: C, 65.39; H, 4.88; N, 17.48.

2-(4-Methylphenyl)-9-[2-(4-phenoxyphenyl)ethyl]-2,6-dihydro[1,2,4]triazolo[4,3-o]-quinazoline-3,5-dione (14f) was prepared and purified according to the procedure described for 14a, starting from 13f. The reaction yielded 14f (80%) as a white solid (mp: 213° C.).

$^1$H NMR (400 MHz, DMSO-d6) δ 11.40 (1H, s), 7.83 (3H, m), 7.44 (1H, d, J=8.5 Hz), 7.33 (3H, m), 7.27 (2H, d, J=8.2 Hz), 7.11 (3H, m), 6.94 (4H, m), 2.35 (3H, s); $^{13}$C NMR (100 MHz, DMSO-d6) δ 157.1, 154.6, 146.8, 143.9, 140.5, 136.9, 136.5, 135.4, 135.0, 134.8, 133.0, 130.0, 130.0, 130.0, 130.0, 129.5, 129.5, 123.1, 121.9, 118.9, 118.9, 118.8, 118.8, 118.2, 118.2, 115.7, 109.0, 36.4, 36.3, 20.5; HRMS (ESI): for $C_{30}H_{25}N_4O_3$ calcd: 489.1927 [M+H]. found: 489.1929. Anal. Calcd. for $C_{30}H_{24}N_4O_3$: C, 73.76; H, 4.95; N, 11.47. Found: C, 73.96; H, 4.94; N, 11.53;

9-[2-(Biphen-4-yl)ethyl)]-2-(4-methylphenyl)-2,6-dihydro[1,2,4]triazolo[4,3-c]-quinazoline-3,5-dione (14g) was prepared and purified according to the procedure described for 14a, starting from 13g. The reaction yielded 14g (98%) as a white solid (mp: 345° C.).

$^1$H NMR (500 MHz, DMSO-d6) δ 11.07 (1H, s), 7.82 (3H, m), 7.62 (2H, d, J=6.3 Hz), 7.56 (2H, d, J=6.5 Hz), 7.43 (3H, m), 7.31 (5H, m), 7.18 (1H, d, J=7.9 Hz), 3.01 (4H, m), 2.36 (3H, s); $^{13}$C NMR (125 MHz, DMSO-d6) δ 146.2, 143.1, 139.9, 139.8, 139.7, 137.5, 136.4, 135.0, 134.6, 134.5, 132.3, 128.8, 128.8, 128.3, 128.3, 128.1, 128.1, 126.4, 125.9, 125.9, 125.8, 125.8, 121.3, 118.8, 118.8, 115.2, 108.5, 35.7, 35.3, 19.8; HRMS (ESI): for $C_{30}H_{25}N_4O_2$ calcd: 473.1978 [M+H]. found: 473.1981. Anal. Calcd. for $C_{30}H_{24}N_4O_2$: C, 76.25; H, 5.12; N, 11.86. Found: C, 76.30; H, 5.19; N, 11.66.

9-[2-(3-hydroxyphenyl)ethyl)-2-(4-Methylphenyl)-2,6-dihydro[1,2,4]triazolo[4,3-c]-quinazoline-3,5-dione (14i) was prepared and purified according to the procedure described for 14a, starting from 13g. The reaction yielded 14g (96%) as a white solid [mp: 300° C. (decomp.)].

$^1$H NMR (400 MHz, DMSO-d$_6$) δ 11.48 (1H, s), 9.41 (1H, s), 7.83 (2H, d, J=8.3 Hz), 7.79 (1H, s), 7.41 (1H, d, J=8.4 Hz), 7.31 (2H, d, J=8.3 Hz), 7.18 (1H, d, J=8.4 Hz), 7.03 (1H, dd, J=7.5 and 8.0 Hz), 6.65 (2H, m), 6.59 (1H, bd, J=7.0 Hz), 2.84 (4H, m), 2.33 (3H, s); $^{13}$C NMR (100 MHz, DMSO-d$_6$) δ 157.5, 146.8, 143.9, 142.6, 140.6, 137.0, 135.1, 134.9, 133.0, 129.6, 129.6, 129.2, 126.9, 121.8, 119.1, 119.0, 119.0, 115.8, 115.5, 113.0, 109.1, 37.1, 36.2, 20.6; HRMS (ESI): for $C_{24}H_{21}N_4O_3$ calcd: 413.1614 [M+H]. found: 413.1619. Anal. Calcd. for $C_{24}H_{20}N_4O_3$: C, 69.89; H, 4.89; N, 13.58. Found: C, 70.06; H, 4.81; N, 13.38.

Tributyl-(methyl-3-thiophene)tin (15c)

3-(Bromomethyl)-thiophene was prepared as previously reported: Magnesium turnings (170 mg, 7.0 mmol) in 3 mL of tetrahydrofuran were added to the thiophene (620 mg, 3.5 mmol) and the mixture was heated at 35° C. for 1 h and then cooled to room temperature. The Gringard solution obtained was treated with a solution of tributyltin chloride (0.760 mL, 2.8 mmol) in 3 mL of tetrahydrofuran and stirred at room temperature for 1 h. The mixture was poured onto a saturated aqueous NH$_4$Cl solution and extracted with EtOAc. The organic layer was washed with brine, dried over MgSO$_4$, concentrated and purified by chromatography on a silica gel column. Elution with n-heptane/EtOAc (100:1) as eluent yielded 15c as a clear oil (490 mg, 36%).

$^1$H NMR (400 MHz, CDCl$_3$) δ 7.13 (1H, dd, J=4.9 and 2.95 Hz), 6.77 (1H, dd, J=4.9 and 1.33 Hz), 6.62 (1H, m), 2.33 (2H, s), 1.44 (6H, m), 1.27 (6H, m), 0.88 (9H, m), 0.83 (6H, m), $^{13}$C NMR (100 MHz, CDCl$_3$) δ 142.9, 128.7, 125.1, 115.8, 29.2, 27.5, 17.7, 13.9, 9.6.

9-Benzyl-2-(4-methylphenyl)-2,6-dihydro[1,2,4] triazolo[4,3-c]quinazoline-3,5-dione (16a)

To a stirred solution of benzyltributyltin (69 mg, 0.184 mmol) and 8a (19.5 mg, 0.0525 mmol) in a mixture of 2 mL of DMF and 1 mL of NEt$_3$, was added Pd(PPh$_3$)$_4$ (6.0 mg, 5.3 μmol). The seal tube was sealed under argon and the mixture was stirred at 110° C. for 18 h. The reaction the mixture was cooled and concentrated to dryness in vacuo and the crude product was purified by chromatography on a silica gel column. Elution with n-heptane/EtOAc (2:1) as eluent yielded 16a as a white solid (13 mg, 65%). mp: 299° C., $^1$H NMR (500 MHz, DMSO-d$_6$, 340 K) δ 7.82 (3H, m), 7.43 (1H, d, J=8.0 Hz), 7.29 (5H, m), 7.20 (1H, m), 7.15 (1H, d, J=8.0 Hz), 4.01 (2H, s), 2.34 (3H, s); $^{13}$C NMR (125 MHz, DMSO-d$_6$, 340 K) δ 146.4, 143.4, 140.5, 140.1, 136.3, 135.3, 134.8, 134.6, 132.8, 129.1, 129.1, 128.3, 128.3, 128.1, 128.1, 125.8, 121.8, 118.9, 118.9, 115.6, 108.9, 39.9, 20.1; HRMS (ESI): for $C_{23}H_{19}N_4O_2$ calcd: 383.1508 [M+H]. found: 383.1512. Anal. Calcd. for $C_{23}H_{19}N_4O_2$: C, 72.24; H, 4.74; N, 14.65. Found: C, 72.44; H, 4.62; N, 14.49.

9-(3-Fluorobenzyl)-2-(4-methylphenyl)-2,6-dihydro[1,2,4]triazolo[4,3-c]quinazoline-3,5-dione (16b) was prepared and purified according to the procedure described for 16a, starting from 8a and (3-fluorobenzyl)tributyltin. The reaction yielded 16b (70%) as a white solid (mp: 324° C.).

$^1$H NMR (400 MHz, DMSO-$d_6$) δ 11.37 (1H, s), 7.86 (1H, s), 7.83 (2H, d, J=8.2 Hz), 7.46 (d, J=8.2 Hz), 7.33 (3H, m), 7.13 (3H, m), 7.02 (1H, t, J=8.3 Hz), 4.04 (2H, s), 2.34 (3H, s); $^{13}$C NMR (100 MHz, DMSO-$d_6$) δ162.2 (d, J=243.5 Hz), 146.7, 144.0 (d, J=7.3 Hz), 143.9, 140.4, 136.1, 135.7, 135.0, 134.8, 133.2, 130.4 (d, J=8.4 Hz), 129.5, 129.5, 124.8 (d, J=2.6 Hz), 122.2, 118.9, 118.9, 116.0, 115.4 (d, J=21.1 Hz), 112.9 (d, J=20.9 Hz), 109.3, 40.4, 20.5; HRMS (ESI): for $C_{23}H_{18}N_4O_2F$ calcd: 401.1414 [M+H]. found: 401.1417. Anal. Calcd. for $C_{23}H_{17}N_4O_2F$: C, 68.99; H, 4.28; N, 13.99. Found: C, 68.78; H, 4.49; N, 13.81.

2-(4-Methylphenyl)-9-(3-thienylmethyl)-2,6-dihydro[1,2,4]triazolo[4,3-c]quinazoline-3,5-dione (16c) was prepared and purified according to the procedure described for 16a, starting from 8a and 15c. The reaction yielded 16c (62%) as a white solid (mp: 287° C.).

$^1$H NMR (400 MHz, DMSO-$d_6$) δ 11.37 (1H, s), 7.82 (3H, m), 7.46 (2H, m), 7.32 (2H, d, J=8.3 Hz), 7.25 (1H, bs), 7.12 (1H, d, J=8.3 Hz), 6.98 (1H, d, J=4.5 Hz), 4.01 (2H, s), 2.34 (3H, s); $^{13}$C NMR (100 MHz, DMSO-$d_6$) δ 146.7, 143.9, 141.1, 140.5, 136.3, 135.5, 135.0, 134.8, 133.1, 129.5, 129.5, 128.4, 126.4, 122.0, 121.6, 121.6, 118.9, 115.9, 109.2, 34.8, 20.5; HRMS (ESI): for $C_{21}H_{17}N_4O_2S$ calcd: 389.1072 [M+H]. found: 389.1074. Anal. Calcd. for $C_{21}H_{16}N_4O_2S$: C, 64.93; H, 4.15; N, 14.42. Found: C, 64.72; H, 4.33; N, 14.63.

Benzyl (2E)-3-[2-(4-methylphenyl)-3,5-dioxo-2,6-dihydro[1,2,4]triazolo[4,3-c]quinazolin-9-yl]acrylate (17)

To a stirred solution of benzyl acrylate (44 µg, 0.274 mmol) and 8a (50.6 mg, 0.137 mmol) in a mixture of 8 mL of DMF and 4 mL of NEt$_3$, was added Pd(OAc)$_2$ (3.06 mg, 13.7 mmol) and triphenylphosphine (7.14 mg, 27.4 µmol) in a seal tube. The tube was sealed under argon and the mixture was stirred at 120° C. for 15 h. The mixture was cooled and concentrated to dryness in vacuo and the crude product was precipitated from acetone to give 17 as a white solid (29 mg, 47%). mp: 242° C.

$^1$H NMR (400 MHz, DMSO-$d_6$) δ 11.58 (1H, bs), 8.29 (1H, s), 7.95 (1H, bd, J=8.5 Hz), 7.87 (2H, d, J=8.3 Hz), 7.78 (1H, d, J=16.0 Hz), 7.35-7.46 (5H, m), 7.32 (2H, d, J=8.3 Hz), 7.19 (1H, d, J=8.5 Hz), 6.74 (1H, d, J=16.0 Hz) 5.23 (2H, s,), 2.35 (3H, s); $^{13}$C NMR (100 MHz, DMSO-$d_6$) δ 166.0, 146.7, 144.0, 143.5, 140.2, 139.5, 136.2, 135.0, 134.8, 131.7, 131.5, 129.5, 129.5, 129.0, 128.5, 128.5, 128.1, 128.1, 123.2, 118.8, 118.8, 117.5, 116.7, 109.8, 65.6, 20.5, HRMS (ESI): for $C_{26}H_{21}N_4O_4$ calcd: 453.1563 [M+H]. found: 453.1559.

3-[2-(4-Methylphenyl)-3,5-dioxo-2,6-dihydro[1,2,4]triazolo[4,3-c]quinazolin-9-yl]propanoic acid (18) was prepared and purified according to the procedure described for 14a, starting from 17. The reaction yielded 18 (71%) as a white solid (mp: 275° C.).

$^1$H NMR (400 MHz, DMSO-$d_6$) δ 11.43 (1H, bs), 7.85 (2H, d, J=8.4 Hz), 7.82 (1H, bs), 7.44 (1H, bd, J=8.2 Hz), 7.32 (2H, d, J=8.4 Hz), 7.14 (1H, d, J=8.2 Hz), 3.58 (1H, s, COOH), 2.90 (2H, m), 2.68 (1H, m), 2.56 (1H, m), 2.34 (3H, s); $^{13}$C NMR (100 MHz, DMSO-$d_6$) δ 172.5, 146.8, 143.9, 140.5, 135.9, 135.0, 134.9, 134.8, 132.9, 129.5, 129.5, 121.8, 118.9, 118.9, 115.8, 109.1, 34.7, 29.5, 20.5; HRMS (ESI): for $C_{19}H_{17}N_4O_4$ calcd: 365.125 [M+H]. found: 365.130 Anal. Calcd. for $C_{19}H_{17}N_4O_4$: C, 62.63; H, 4.43; N, 15.38. Found: C, 65.8; H, 4.34; N, 15.99.

Receptor Binding

Affinity of test substances for the benzodiazepine receptor was determined in vitro by displacement of $^3$H-flumazenil in rat cortical tissue. The results are shown in Table 1.

TABLE 1

$K_i$ Values of novel benzodiazepine analogues tested on $^3$H-Flumazenil binding in vitro rat cortical membranes

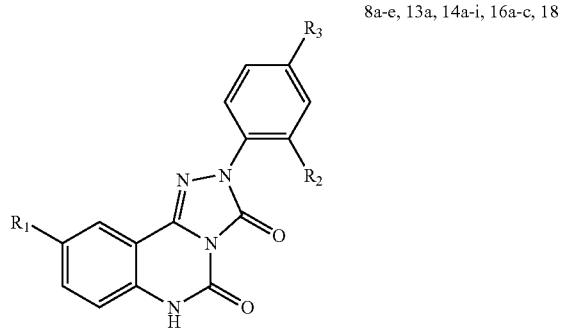

8a-e, 13a, 14a-i, 16a-c, 18

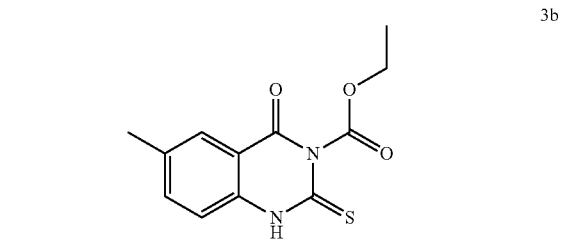

3b

| Compds | Name | $R_1$ | $R_2$ | $R_3$ | $K_i$ value (nM)[a] |
|---|---|---|---|---|---|
| 3b | JN3-42 | | | | >30 000 |
| 8a | JN7-135 | Br— | H— | H— | 0.24 ± 0.07 |
| 8b | AC1 | Br— | H— | Me— | 0.47 ± 0.09 |
| 8c | JN7-106 | Br— | H— | Cl— | 0.6 ± 0.26 |
| 8d | JN7-119 | Br— | F— | H— | 0.20 ± 0.07 |
| 8e | RG-219 | CH$_3$— | H— | H— | 0.62 ± 0.13 |
| 13a | JN6-63 | phenyl-C≡C— | H— | Me— | 40 ± 11 |
| 14a | JN7-144 | phenyl-CH$_2$CH$_2$— | H— | Me— | 4.0 ± 1.2 |
| 14b | JN7-159 | (3-thiophenyl)-CH$_2$CH$_2$— | H— | Me— | 0.94 ± 0.27 |
| 14c | JN7-146 | (2-pyridyl)-CH$_2$CH$_2$— | H— | Me— | 0.53 ± 0.11 |
| 14d | JN7-156 | (3-pyridyl)-CH$_2$CH$_2$— | H— | Me— | 0.20 ± 0.04 |
| 14e | JN7-155 | (4-pyridyl)-CH$_2$CH$_2$— | H— | Me— | 0.17 ± 0.03 |
| 14f | JN8-8 | (4-PhOPh)-CH$_2$CH$_2$— | H— | Me— | 123 ± 12 |
| 14g | JN8-35 | (4-biphenyl)-CH$_2$CH$_2$— | H— | Me— | 1570 ± 150[b] |
| 14i | JN8-60 | (3-hyroxyphenyl)-CH$_2$CH$_2$— | H— | Me— | 6.2 |
| 16a | JN7-69 | benzyl- | H— | Me— | ca 1 nM |
| 16b | JN7-140 | 3-fluorophenyl-CH$_2$— | H— | Me— | 2.1 ± 0.3 |
| 16c | JN7-139 | (3-thiophenyl)-CH$_2$— | H— | Me— | 0.23 ± 0.18 |
| 18 | JN8-77 | HOOC—CH$_2$CH$_2$— | H— | Me— | 1.4 |

[a]Each $K_i$ value is the mean ± SD of three determinations.
[b]Desolvation problems.

Results and Discussion

Compound 3b has previously been suggested as a potential BZD receptor ligand. It was proposed to bind similar to the triazoloquinazolinones with NH(4), the 4-carbonylic oxygen, and the 3-carbonylate oxygen acting as hydrogen bond donor to A$_2$ and hydrogen bond acceptor to H$_2$ and H$_1$ in the pharmacophore model representation, respectively.

The low affinity for 3b can most likely be attributed to the sterical repulsion between the carboxylate group chain and the sulfur atom, which forces the molecule to adopt an inactive non-planar conformation. The triazoloquinazolines are structurally related to the 2-arylpyrazoloquinolines and substitution of the latter in the 4'-position with H—, Cl— and MeO— as well as substitution in the 2'-position with —F has resulted in subnanomolar affinities. Compounds 8a-e all display similar subnanomolar affinities and in terms of binding strength the 4'-Me substituent was chosen arbitrary as lead structure for further substitution in the 9-position. Not surprisingly, the difference between a methyl- (8e) and a bromo- (8b) substituent in the 9-position is small. Among the most potent compounds presented in this study are the pyridyl decorated compounds 14a-c. Despite considerably higher desolvation energy, the pyridyl compounds display up to 24-fold higher affinity compared to the phenyl compounds 14a and 14i. This may be explained by a partial solvatisation of the pyridyl group and as a consequence no additional desolvation energy would be lost upon binding to the receptor. The results support the hypothesis that the interface region is a water filled channel-like cavity, which previously have been proposed to be located in this area. In particular, a high affinity may be expected for a well solvated flexible side-chain preferably.

This is also believed to be further supported by the high affinity of carboxylic acid derivative 18 (1.4 nM). An interesting observation is the 5-fold higher affinity for the methylene linked thiophene 16c compared to phenyl 16a. A similar 4-fold difference in potency is also observed among the ethylene linked compounds in favor of the thiophene 14a over phenyl 14b. This difference is also consistent among the 3-fluorophenyl compound 16b and hydroxyphenyl compound 14i. The thiophene and phenyl groups have somewhat different electronic properties, but exhibit only a slight difference in intrinsic volume.

Furthermore, it is clear that the large biphenyl- and phenoxy phenyl group are discriminated, indicating a sterical repulsive interaction further out in the "interface". Worth noticing is also the large tolerance for rigid planar substituents such as the phenylacetylene 13a, with an affinity of 40 nM. Although not favored the well tolerable non-flexible substituent to some extent displays the large extension of the cavity in the interface region.

Within the scope of the invention are also salts of the compounds of formula I. Generally, pharmaceutically acceptable salts of compounds of the present invention are obtained using standard procedures well known in the art, for example, by reacting a sufficiently basic compound, for example an alkyl amine with a suitable acid, for example, HCl or acetic acid, to afford a salt with a physiologically acceptable anion. It is also possible to make a corresponding alkali metal (such as sodium, potassium, or lithium) or an alkaline earth metal (such as a calcium) salt by treating a compound of the present invention having a suitably acidic proton, such as a carboxylic acid or a phenol, with one equivalent of an alkali metal or alkaline earth metal hydroxide or alkoxide (such as the ethoxide or methoxide), or a suitably basic organic amine (such as choline or meglumine) in an aqueous medium, followed by conventional purification techniques. Additionally, quaternary ammonium salts can be prepared by the addition of alkylating agents, for example, to neutral amines.

In one embodiment of the present invention, the compound of formula I may be converted to a pharmaceutically acceptable salt or solvate thereof, particularly, an acid addition salt such as a hydrochloride, hydrobromide, phosphate, acetate, fumarate, maleate, tartrate, citrate, methanesulphonate or p-toluenesulphonate.

Specific examples of the present invention include the following compounds, their pharmaceutically acceptable salts, hydrates, solvates, optical isomers, and combinations thereof:

Pharmaceutical Composition

The compounds of the present invention may be formulated into conventional pharmaceutical composition comprising a compound of formula I, or a pharmaceutically acceptable salt or solvate thereof, in association with a pharmaceutically acceptable carrier or excipient. The pharmaceutically acceptable carriers can be either solid or liquid. Solid form preparations include, but are not limited to, powders, tablets, dispersible granules, capsules, cachets, and suppositories.

A solid carrier can be one or more substances, which may also act as diluents, flavoring agents, solubilizers, lubricants, suspending agents, binders, or tablet disintegrating agents. A solid carrier can also be an encapsulating material.

In powders, the carrier is a finely divided solid, which is in a mixture with the finely divided compound of the invention, or the active component, in tablets, the active component is mixed with the carrier having the necessary binding properties in suitable proportions and compacted in the shape and size desired.

For preparing suppository compositions, a low-melting wax such as a mixture of fatty acid glycerides and cocoa butter is first melted and the active ingredient is dispersed therein by, for example, stirring. The molten homogeneous mixture is then poured into convenient sized moulds and allowed to cool and solidify.

Suitable carriers include, but are not limited to, magnesium carbonate, magnesium stearate, talc, lactose, sugar, pectin, dextrin, starch, tragacanth, methyl cellulose, sodium carboxymethyl cellulose, low-melting wax, cocoa butter, and the like.

The term composition is also intended to include the formulation of the active component with encapsulating material as a carrier providing a capsule in which the active component (with or without other carriers) is surrounded by a carrier which is thus in association with it. Similarly, cachets are included.

Tablets, powders, cachets, and capsules can be used as solid dosage forms suitable for oral administration.

Liquid form compositions include solutions, suspensions, and emulsions. For example, sterile water or water propylene glycol solutions of the active compounds may be liquid preparations suitable for parenteral administration. Liquid compositions can also be formulated in solution in aqueous polyethylene glycol solution.

Aqueous solutions for oral administration can be prepared by dissolving the active component in water and adding suitable colorants, flavoring agents, stabilizers, and thickening agents as desired. Aqueous suspensions for oral use can be made by dispersing the finely divided active component in water together with a viscous material such as natural synthetic gums, resins, methyl cellulose, sodium carboxymethyl cellulose, and other suspending agents known to the pharmaceutical formulation art. Exemplary compositions intended for oral use may contain one or more coloring, sweetening, flavoring and/or preservative agents.

Depending on the mode of administration, the pharmaceutical composition will include from about 0.05% w (percent by weight) to about 99% w, more particularly, from about 0.10% w to 50% w, of the compound of the invention, all percentages by weight being based on the total weight of the composition. A therapeutically effective amount for the practice of the present invention can be determined by one of ordinary skill in the art using known criteria including the age, weight and response of the individual patient, and interpreted within the context of the disease which is being treated or which is being prevented.

The invention claimed is:

1. A compound selected from the group consisting of:
9-Bromo-2-(4-methylphenyl)-2,6-dihydro[1,2,4]triazolo [4,3-c]quinazoline-3,5-dione,
9-Bromo-2-phenyl-2,6-dihydro[1,2,4]triazolo[4,3-c] quinazoline-3,5-dione,
9-Bromo-2-(4-chlorophenyl)-2,6-dihydro[1,2,4]triazolo [4,3-c]quinazoline-3,5-dione,
9-Bromo-2-(2-fluorophenyl)-2,6-dihydro[1,2,4]triazolo [4,3-c]quinazoline-3,5-dione,
9-Methyl-2-phenyl-2,6-dihydro[1,2,4]triazolo[4,3-c] quinazoline-3,5-dione,
2-(4-Methylphenyl)-9-phenyethynyl)-2,6-dihydro[1,2,4] triazolo[4,3-c]-quinazoline-3,5-dione,
2-(4-Methylphenyl)-9-(2-phenylethyl)-2,6-dihydro[1,2,4] triazolo[4,3-c]-quinazoline-3,5-dione,
2-(4-Methylphenyl)-9-[2-(3-thienyl)ethyl]-2,6-dihydro[1, 2,4]triazolo[4,3-c]-quinazoline-3,5-dione,
2-(4-Methylphenyl)-9-[2-(2-pyridyl)ethyl]-2,6-dihydro [1,2,4]triazolo[4,3-c]-quinazoline-3,5-dione,
2-(4-Methylphenyl)-9-[2-(3-pyridyl)ethyl]-2,6-dihydro [1,2,4]triazolo[4,3-c]-quinazoline-3,5-dione,
2-(4-Methylphenyl)-9-[2-(4-pyridyl)ethyl]-2,6-dihydro [1,2,4]triazolo[4,3-c]-quinazoline-3,5-dione,
2-(4-Methylphenyl)-9-[2-(4-phenoxyphenyl)ethyl]-2,6-dihydro[1,2,4]triazolo[4,3-c]-quinazoline-3,5-dione,
9-[2-(Biphen-4-yl)ethyl)]-2-(4-methylphenyl)-2,6-dihydro[1,2,4]triazolo[4,3-c]-quinazoline-3,5-dione,
9-[2-(3-hydroxyphenyl)ethyl]-2-(4-Methylphenyl)-2,6-dihydro[1,2,4]triazolo[4,3-c]-quinazoline-3,5-dione,
9-Benzyl-2-(4-methylphenyl)-2,6-dihydro[1,2,4]triazolo [4,3-c]quinazoline-3,5-dione,
9-(3-Fluorobenzyl)-2-(4-methylphenyl)-2,6-dihydro[1,2, 4]triazolo[4,3-c]quinazoline-3,5- dione,
2-(4-Methylphenyl)-9-(3-thienylmethyl)-2,6-dihydro[1,2, 4]triazolo[4,3-c]quinazoline-3,5-dione,
3-[2-(4-Methylphenyl)-3,5-dioxo-2,6-dihydro[1,2,4]triazolo (4,3-c]quinazolin-9-yl]propanoic acid, and
pharmaceutically acceptable salts thereof.

2. Pharmaceutical composition comprising as an active ingredient one or more of the compound selected from the group consisting of:
9-Bromo-2-(4-methylphenyl)-2,6-dihydro[1,2,4]triazolo [4,3-c]quinazoline-3,5-dione,
9-Bromo-2-phenyl-2,6-dihydro[1,2,4]triazolo[4,3-c] quinazoline-3,5-dione,
9-Bromo-2-(4-chlorophenyl)-2,6-dihydro[1,2,4]triazolo [4,3-c]quinazoline-3,5-dione,
9-Bromo-2-(2-fluorophenyl)-2,6-dihydro[1,2,4]triazolo [4,3-c]quinazoline-3,5-dione,
9-Methyl-2-phenyl-2,6-dihydro[1,2,4]triazolo[4,3-c] quinazoline-3,5-dione,
2-(4-Methylphenyl)-9-phenyethynyl)-2,6-dihydro[1,2,4] triazolo[4,3-c]-quinazoline-3,5-dione,
2-(4-Methylphenyl)-9-(2-phenylethyl)-2,6-dihydro[1,2,4] triazolo[4,3-c]-quinazoline-3,5-dione,
2-(4-Methylphenyl)-9-[2-(3-thienyl)ethyl]-2,6-dihydro[1, 2,4]triazolo[4,3-c]-quinazoline-3,5-dione,
2-(4-Methylphenyl)-9-[2-(2-pyridyl)ethyl]-2,6-dihydro [1,2,4]triazolo[4,3-c]-quinazoline-3,5-dione,
2-(4-Methylphenyl)-9-[2-(3-pyridyl)ethyl]-2,6-dihydro [1,2,4]triazolo[4,3-c]-quinazoline-3,5-dione,
2-(4-Methylphenyl)-9-[2-(4-pyridyl)ethyl]-2,6-dihydro [1,2,4]triazolo[4,3-c]-quinazoline-3,5-dione,
2-(4-Methylphenyl)-9-[2-(4-phenoxyphenyl)ethyl]-2,6-dihydro[1,2,4]triazolo[4,3-c]-quinazoline-3,5-dione,
9-[2-(Biphen-4-yl)ethyl)]-2-(4-methylphenyl)-2,6-dihydro[1,2,4]triazolo[4,3-c]-quinazoline-3,5-dione,
9-[2-(3-hydroxyphenyl)ethyl]-2-(4-Methylphenyl)-2,6-dihydro[1,2,4]triazolo[4,3-c]-quinazoline-3,5-dione,
9-Benzyl-2-(4-methylphenyl)-2,6-dihydro[1,2,4]triazolo [4,3-c]quinazoline-3,5-dione,
9-(3-Fluorobenzyl)-2-(4-methylphenyl)-2,6-dihydro[1,2, 4]triazolo[4,3-c]quinazoline-3,5-dione,
2-(4-Methylphenyl)-9-(3-thienylmethyl)-2,6-dihydro[1,2, 4]triazolo[4,3-c]quinazoline-3,5-dione,
3-[2-(4-Methylphenyl)-3,5-dioxo-2,6-dihydro[1,2,4]triazolo (4,3-c]quinazolin-9-yl]propanoic acid, and
pharmaceutically acceptable salts thereof.

* * * * *